US010456453B2

(12) United States Patent
McDonagh et al.

(10) Patent No.: US 10,456,453 B2
(45) Date of Patent: *Oct. 29, 2019

(54) USE OF ANGIOGENIN OR ANGIOGENIN AGONISTS FOR TREATING DISEASES AND DISORDERS

(71) Applicants: AGRICULTURE VICTORIA SERVICES PTY LTD, Attwood (AU); SAPUTO DAIRY AUSTRALIA PTY LIMITED, Allansford (AU)

(72) Inventors: Matthew McDonagh, Williamstown (AU); Benjamin Cocks, Viewbank (AU); Angus Tester, Moonee Ponds (AU); Peter Hobman, Melbourne (AU); Andrew Brown, Point Cook (AU); Michelle Rowney, Port Campbell (AU)

(73) Assignees: AGRICULTURE VICTORIA SERVICES PTY LTD, Attwood (AU); SAPUTO DAIRY AUSTRALIA PTY LIMITED, Allansford (AU)

(*) Notice: Subject to any disclaimer, the term of this patent is extended or adjusted under 35 U.S.C. 154(b) by 10 days.

This patent is subject to a terminal disclaimer.

(21) Appl. No.: 15/703,203

(22) Filed: Sep. 13, 2017

(65) Prior Publication Data

US 2018/0000908 A1    Jan. 4, 2018

Related U.S. Application Data

(63) Continuation of application No. 14/810,983, filed on Jul. 28, 2015, now Pat. No. 9,789,168, which is a continuation of application No. 12/992,501, filed as application No. PCT/AU2009/000603 on May 14, 2009, now Pat. No. 9,119,818.

(30) Foreign Application Priority Data

May 14, 2008 (AU) ................. 2008902365
May 14, 2008 (AU) ................. 2008902372

(51) Int. Cl.
| | |
|---|---|
| *A61K 38/46* | (2006.01) |
| *A61K 38/17* | (2006.01) |
| *A61K 38/18* | (2006.01) |
| *A23K 20/142* | (2016.01) |
| *A23L 33/19* | (2016.01) |
| *A61K 9/00* | (2006.01) |
| *A61K 35/20* | (2006.01) |

(52) U.S. Cl.
CPC .......... *A61K 38/465* (2013.01); *A23K 20/142* (2016.05); *A23L 33/19* (2016.08); *A61K 38/1709* (2013.01); *A61K 38/1891* (2013.01); *A61K 35/20* (2013.01); *C12Y 301/27* (2013.01)

(58) Field of Classification Search
None
See application file for complete search history.

(56) References Cited

U.S. PATENT DOCUMENTS

| | | | |
|---|---|---|---|
| 5,171,845 | A | 12/1992 | Spik et al. |
| 5,596,082 | A | 1/1997 | Kussendrager et al. |
| 6,010,698 | A | 1/2000 | Kussendrager et al. |
| 7,659,243 | B2 | 2/2010 | Greenway et al. |
| 8,067,360 | B2 | 11/2011 | Knopf et al. |
| 8,114,969 | B2 | 2/2012 | Vincent et al. |
| 8,440,183 | B2 | 5/2013 | Naidu et al. |
| 8,551,547 | B2 | 10/2013 | Brown et al. |
| 9,119,818 | B2 | 9/2015 | McDonagh et al. |
| 9,789,168 | B2 | 10/2017 | McDonagh et al. |
| 2005/0037955 | A1 | 2/2005 | Hooper et al. |
| 2007/0253941 | A1 | 11/2007 | Naidu et al. |
| 2007/0275036 | A1 | 11/2007 | Green, III et al. |
| 2008/0045546 | A1 | 2/2008 | Bouchon et al. |
| 2009/0099128 | A1 | 4/2009 | Wu |
| 2009/0305972 | A1 | 12/2009 | Chahal et al. |
| 2014/0370087 | A1 | 12/2014 | Kim et al. |

FOREIGN PATENT DOCUMENTS

| | | | |
|---|---|---|---|
| EP | 0704218 | A2 | 4/1996 |
| EP | 0786473 | A2 | 7/1997 |
| EP | 0869134 | A1 | 10/1998 |
| JP | H08511236 | A | 11/1996 |
| JP | 10007585 | A | 1/1998 |
| JP | 2003-144095 | A | 5/2003 |
| JP | 2004-331566 | A | 11/2004 |

(Continued)

OTHER PUBLICATIONS

"Comparing Distributions: Z Test," <http://homework.uoregon.edu/pub/class/es202/ztest.html>, retrieved Jun. 8, 2016 (4 pages).
Acharya et al., "Crystal structure of human angiogenin reveals the structural basis for its functional divergence from ribonuclease," Proc Natl Acad Sci USA. 91(8): 2915-19 (1994).
Fedorova et al., "Milk ultrafiltrate as a promising source of angiogenin," Applied Biochemistry and Microbiology 38(2):193-6 (2002).
First Examination Report for Indian Application No. 8876/DELNP/2010, dated Apr. 28, 2017 (9 pages).
Gao et al., "Identification and characterization of follistatin as a novel angiogenin-binding protein," FEBS Lett. 581(28):5505-10 (2007).

(Continued)

*Primary Examiner* — Allison M Fox
(74) *Attorney, Agent, or Firm* — Clark & Elbing LLP

(57) ABSTRACT

The invention provides a method of treating a disorder characterised by elevated or dysregulated myostatin, disorders where the interaction between follistatin and angiogenin can be used to improve function in tissues, neurological diseases or disorders, spinal injuries or diseases, bone diseases or disorders, diseases involving glucose homeostasis, wound healing, neuroprotection, nervous system functional support or managing metabolic diseases, the method comprising administering an effective amount of angiogenin or an angiogenin agonist. Compositions and neutraceuticals comprising angiogenin are also provided.

24 Claims, 10 Drawing Sheets

(56) References Cited

FOREIGN PATENT DOCUMENTS

| | | |
|---|---|---|
| JP | 2005-507637 A | 3/2005 |
| JP | 2007-526337 A | 9/2007 |
| JP | 2009-543868 A | 12/2009 |
| KR | 2005-0091015 A | 9/2005 |
| RU | 2110066 C1 | 4/1998 |
| RU | 2204262 C2 | 5/2003 |
| RU | 2008145662 A | 6/2010 |
| WO | WO-99/23112 A1 | 5/1999 |
| WO | WO-99/58126 A1 | 11/1999 |
| WO | WO-01/00792 A1 | 1/2001 |
| WO | WO-02/052022 A2 | 7/2002 |
| WO | WO-02/068650 A2 | 9/2002 |
| WO | WO-2004/058988 A2 | 7/2004 |
| WO | WO-2004/106491 A2 | 12/2004 |
| WO | WO-2005/072764 A2 | 8/2005 |
| WO | WO-2005/084699 A1 | 9/2005 |
| WO | WO-2006/002106 A2 | 1/2006 |
| WO | WO-2006/054277 A2 | 5/2006 |
| WO | WO-2007/013666 A2 | 2/2007 |
| WO | WO-2007/023479 A2 | 3/2007 |
| WO | WO-2007/075396 A2 | 7/2007 |
| WO | WO-2007/127183 A1 | 11/2007 |
| WO | WO-2008/055310 A1 | 5/2008 |
| WO | WO-2009/043455 A2 | 4/2009 |
| WO | WO-2009/137879 A1 | 11/2009 |
| WO | WO-2009/137880 A1 | 11/2009 |
| WO | WO-2009/137881 A1 | 11/2009 |
| WO | WO-2011/060488 A1 | 5/2011 |
| WO | WO-2011/060489 A1 | 5/2011 |
| WO | WO-2011/063160 A1 | 5/2011 |
| WO | WO-2013/166555 A1 | 11/2013 |
| WO | WO-2013/166557 A1 | 11/2013 |

OTHER PUBLICATIONS

Gao et al., "Mechanisms of action of angiogenin," Acta Biochim Biophys Sin (Shanghai). 40(7):619-24 (2008).

International Search Report for PCT/AU2009/000603, dated Jul. 7, 2009 (3 pages).

Jang et al., "High level production of bovine angiogenin in E. coli by an efficient refolding procedure," Biotechnol Lett. 26(19):1501-4 (2004).

Kieran et al., "Control of motoneuron survival by angiogenin," J Neurosci. 28(52):14056-61 (2008).

Maes et al., "The complete amino acid sequence of bovine milk angiogenin," FEBS Lett. 241(1-2):41-5 (1988).

National Cancer Institute, "Angiogenesis Inhibitors," <http://www.cancer.gov/about-cancer/treatment/types/immunotherapy/angiogenesis-inhibitors-fact-sheet>, retrieved Jun. 10, 2016 (3 pages).

Ng et al., "Inhibition of human immunodeficiency virus type 1 reverse transcriptase, protease and integrase by bovine milk proteins," Life Sci. 69(19):2217-23 (2001).

Office Action for European Application No. 13787726.2, dated Apr. 24, 2017 (6 pages).

Office Action for Korean Application No. 10-2010-7028077, dated Jan. 21, 2016 (9 pages).

Official Action for Russian Application No. 2014149807, dated May 10, 2017 (12 pages).

Olson et al., "A monoclonal antibody to human angiogenin suppresses tumor growth in athymic mice," Cancer Res. 54(17):4576-9 (1994).

Piccoli et al., "Chimeric anti-angiogenin antibody cAb 26-2F inhibits the formation of human breast cancer xenografts in athymic mice," Proc Natl Acad Sci USA. 95(8):4579-83 (1998).

Rustam'yan et al., "Penetration of cow milk angiogenin into the blood of mice after peroral introduction," Biol Bull. 29(2):165-7 (2002).

Subramanian et al., "Human angiogenin is a neuroprotective factor and amyotrophic lateral sclerosis associated angiogenin variants affect neurite extension/pathfinding and survival of motor neurons," Hum Mol Genet. 17(1):130-49 (2008).

Supplementary European Search Report for European Application No. 09745302.1, dated Sep. 7, 2011 (12 pages).

Tsuda et al., "Cancer prevention by bovine lactoferrin and underlying mechanisms—a review of experimental and clinical studies," Biochem Cell Biol. 80(1):131-6 (2002) (10 pages).

van den Berg et al., "Patterns of expression of the Follistatin and Follistatin-like1 genes during chicken heart development: a potential role in valvulogenesis and late heart muscle cell formation," Anat Rec (Hoboken) 290(7):783-7 (2007).

Xu et al., "Angiogenin activates human umbilical artery smooth muscle cells," Biochem Biophys Res Commun. 285(4) 909-14 (2001).

USE OF ANGIOGENIN OR ANGIOGENIN AGONISTS FOR TREATING DISEASES AND DISORDERS

FIELD

The present invention relates to methods for treating muscle disorders, including muscle wasting disorders and methods for improving muscle form by improving muscle function, strength, mass or exercise tolerance. The invention also relates to methods of decreasing fat, improving muscle to fat ratio and treating diseases caused by or involving suboptimal muscle to fat ratio. The invention also relates to treating diseases which can be treated by improving follistatin mediated stimulation of cells.

BACKGROUND

Although muscle has its own progenitor cell for regeneration, lost muscle bulk and strength due to disease and injury are often never completely recovered. Therefore, treatments that can stimulate muscle growth and prevent muscle loss are likely to benefit a significant proportion of the population.

Increase in muscle growth, weight or function is important for treatment of deleterious conditions of the muscle, including, for example, muscle damage, muscle wasting, muscle degeneration, muscle atrophy or reduced rates of muscle repair. Such deleterious conditions of the muscle can result from normal conditions of use or trauma, or quite frequently, through chronic disease states.

In addition to the various muscle disorders that may require treatment, improving muscle to fat ratio so as to have a greater lean mass has been proposed to improve bone density. A correlation between lean mass and higher total body bone density has been shown in mice and in men. Conversely people with higher fat mass have been shown to have reduced bone density. Accordingly improving muscle to fat ratio may improve bone density and be particularly useful in treating bone disorders such as osteoporosis.

Additionally perfectly healthy people may be desirous of improved muscle form or function. It may be desirous to improve a person's weight carrying capacity, endurance, speed, or overall physique, all of which can be achieved by improving muscle mass or function. Additionally, it may be desirous to improve the recovery of muscle from injury or reduce the time a muscle needs to recovery from extended use, for example to reduce the time between training for athletes, thereby improving exercise tolerance.

In animal husbandry, such as involving animals as a food source, methods that increase the proportion and weight of muscle will greatly benefit the industry.

Given the importance of this field a great deal of research is ongoing to develop methods of controlling muscle development or growth. Much work has centred on finding inhibitors of myostatin, as mysotatin, in adults, is a negative regulator of muscle growth (i.e. it suppresses muscle growth).

Follistatin is a 35 kD glycoprotein that is synthesized in many tissues and acts as a binding protein for activin and other members of the TGF (superfamily such as myostatin and some bone morphogenetic proteins. Follistatin is said to be one of several natural myostatin inhibitors, although its physiological role in muscle regulation is currently unknown. Nevertheless, administration of follistatin in muscle has been observed to lead to increased muscle mass, which is believed to be due to its binding and neutralization of myostatin. One of the difficulties of using follistatin as a therapeutic for increasing muscle growth is that follistatin binds other TGF (ligands besides myostatin, for example, activin. Loss of activin activity in mice leads to numerous developmental defects and neonatal death. Activin also limits growth of many types of epithelial tissue, so that inhibition of activin action through administration of follistatin could lead to abnormal growth of these tissues and, eventually, to cancer.

There are currently no approved commercial pharmaceutical means for inhibiting myostatin activity that do not simultaneously alter activin activity. Myostatin antibodies have been developed which bind and neutralize myostatin without binding other TGF (family ligands. However, antibodies may have certain drawbacks that might limit their utility as therapeutics for muscle wasting disorders and certainly the use of antibodies for muscle growth outside the therapeutic arena would be too costly to be commercially useful.

It is an aim of a preferred embodiment of the present invention to address one or more of the above issues and ideally provide a treatment for muscle disorders for improving muscle function, strength, weight and/or exercise tolerance.

All references, including any patents or patent applications, cited in this specification are hereby incorporated by reference. It will be clearly understood that, although a number of prior art publications are referred to herein, this reference does not constitute an admission that any of these documents forms part of the common general knowledge in the art.

SUMMARY

The invention generally provides methods of increasing muscle and reducing fat by administering angiogenin.

A first aspect provides a method of treating a disorder characterised by elevated or dysregulated myostatin in an individual, the method comprising administering an effective amount of angiogenin or an angiogenin agonist.

A second aspect provides a method of treating disorders where the interaction between follistatin and angiogenin can be used to improve function in tissues by administering an effective amount of angiogenin or an angiogenin agonist.

A third aspect provides a method of promoting muscle growth in an individual, the method comprising administering an effective amount of angiogenin or an angiogenin agonist.

A fourth aspect provides a method of improving recovery of muscle from injury or use in an individual, the method comprising administering an effective amount of angiogenin or an angiogenin agonist.

A fifth aspect provides a method of improving muscle strength in an individual, the method comprising administering an effective amount of angiogenin or an angiogenin agonist.

A sixth aspect provides a method of improving exercise tolerance in an individual, the method comprising administering an effective amount of angiogenin or an angiogenin agonist.

A seventh aspect provides a method of increasing the proportion of muscle in an individual, the method comprising administering an effective amount of angiogenin or an angiogenin agonist.

An eighth aspect provides a method of decreasing fat in an individual, the method comprising administering an effective amount of angiogenin or an angiogenin agonist.

A ninth aspect provides a method of decreasing an individual's fat to muscle ratio, the method comprising administering an effective amount of angiogenin or an angiogenin agonist.

Because of the link between muscle mass or muscle to fat ratio and insulin sensitivity/metabolic syndrome (Guo T, Jou W, Chanturiya T, Portas J, Gavrilova O, McPherron A C. PLoS ONE. 2009; 4(3):e4937. Epub 2009 Mar. 19), it is proposed that the methods of the seventh to ninth aspects may treat metabolic syndrome or enhance insulin sensitivity.

A tenth aspect provides a method for improving the bone density of an individual by improving their muscle to fat ratio according to the method of the ninth aspect.

It is proposed that angiogenin is capable of suppressing or reversing the effect of myostatin as a negative regulator of muscle growth.

It is also proposed that myostatin and/or follistatin and/or angiogenin act on cells other than muscle cells; they may act on nerve cells, bone cells (oseoclasts) and endothelial cells.

Accordingly an eleventh aspect provides a method of treating neurological diseases or disorders, spinal injuries or diseases, bone diseases or disorders, diseases involving glucose homeostasis, wound healing, or for providing neuroprotection, nervous system functional support and managing metabolic diseases, the method comprising administering an effective amount of angiogenin or an angiogenin agonist.

Whilst it is proposed that administration of angiogenin may act together with endogenous follistatin, angiogenin or an angiogenin agonist administered with follistatin (either simultaneously or sequentially) was shown by the inventors to have a more than additive effect compared to administration of follistatin alone or angiogenin alone.

It will be appreciated that the converse of the inventors' findings will be true, in that inhibitors or antagonists of angiogenin may be useful for treating diseases or conditions in which a reduction in muscle growth or mass or an increase in fat or fat to muscle ratio or increased myostatin is desired.

The inventors were studying the effect of bovine angiogenin extracted from milk on human cells. They determined that bovine angiogenin is capable of inducing vascular development of human umbilical vein endothelial cells (HUVEC) on matrigel in the same manner as human vascular endothelial growth factor (VEGF).

The inventors then tested the effect of bovine angiogenin extracted from milk in normal mice. The test group exhibited increased quadricep muscle weight and reduced abdominal fat pad weight when fed a diet including bovine angiogenin. The demonstrated role of angiogenin in increasing lean muscle mass and decreasing fat mass indicates that methods involving administering angiogenin or an angiogenin agonist have a broad variety of applications where an increase in muscle tissue would be therapeutically beneficial, such as in livestock production, muscle disorders and for general fitness and physique. The invention may also be useful for treating diseases and disorders related to metabolism and adipose tissue.

The inventors finding is particularly surprising given the teaching of the prior art to administer follistatin to increase muscle mass and reduce fat mass. Without wishing to be bound by theory the inventors propose that angiogenin and follistatin stimulate myotube formation and that myostatin significantly inhibits myotube formation. Angiogenin is proposed to substantially reverse the effect of myostatin. The inventors propose that the interaction between angiogenin and follistatin is a mechanism that is of importance for stimulation, proliferation and development of cell types other than muscle alone. Therefore, administration of angiogenin can be used to treat conditions where improving follistatin mediated effects on cells is beneficial to treatment of disease or condition.

The suggestion that mechanism of action of angiogenin on muscle growth and fat loss is via its interaction with follistatin is supported by the inventors' in vitro studies, where treatment of muscle myoblasts with either angiogenin or follistatin does not stimulate muscle growth over control, whereas administration of both angiogenin and follistatin does.

In one embodiment of any one of the first to eleventh aspects angiogenin or angiogenin agonist is administered with follistatin.

In one embodiment of any one of the first to eleventh aspects angiogenin or angiogenin agonist is administered orally.

In one embodiment of any one of the first to eleventh aspects angiogenin or angiogenin agonist is administered orally and follistatin is administered parentally.

A twelfth aspect provides a composition comprising angiogenin or an angiogenin agonist and follistatin.

In an embodiment of any of the first to twelfth aspects the angiogenin is recombinant angiogenin, preferably human or bovine recombinant angiogenin.

In an embodiment of any of the first to twelfth aspects the angiogenin is provided as an enriched extract from milk or plasma, particularly from bovine milk or from bovine or human plasma. Such an enriched extract is an angiogenin agonist, in that it is not pure angiogenin but provides angiogenin activity.

Follistatin used in the methods or composition may be recombinant or provided as an enriched extract from milk or plasma, particularly from bovine milk or from bovine or human plasma.

A thirteenth aspect provides a composition, food supplement or neutraceutical comprising angiogenin or an angiogenin agonist for treating a disorder characterised by elevated myostatin, for treating disorders where the interaction between follistatin and angiogenin can be used to improve function in tissues, for promoting muscle growth, for improving recovery of muscle from injury or use, for improving muscle strength, for improving exercise tolerance, for increasing the proportion of muscle, for decreasing fat, for decreasing an individual's fat to muscle ratio, for treating neurological diseases or disorders, for treating spinal injuries or diseases, for treating bone diseases or disorders, for treating diseases involving glucose homeostasis, for wound healing, or for providing neuroprotection, nervous system functional support, managing metabolic diseases and/or increasing the bone density of an individual.

A fourteenth aspect provides use of angiogenin or an angiogenin agonist in the manufacture of a medicament for treating a disorder characterised by elevated myostatin, for treating disorders where the interaction between follistatin and angiogenin can be used to improve function in tissues, for promoting muscle growth, for improving recovery of muscle from injury or use, for improving muscle strength, for improving exercise tolerance, for increasing the proportion of muscle, for decreasing fat, for decreasing an individual's fat to muscle ratio, and/or increasing the bone density of an individual.

In an embodiment of the fourteenth aspect the medicament also comprises follistatin.

In another embodiment of the fourteenth aspect the medicament is for administering to an individual being treated with follistatin.

DETAILED DESCRIPTION

Figure 1:
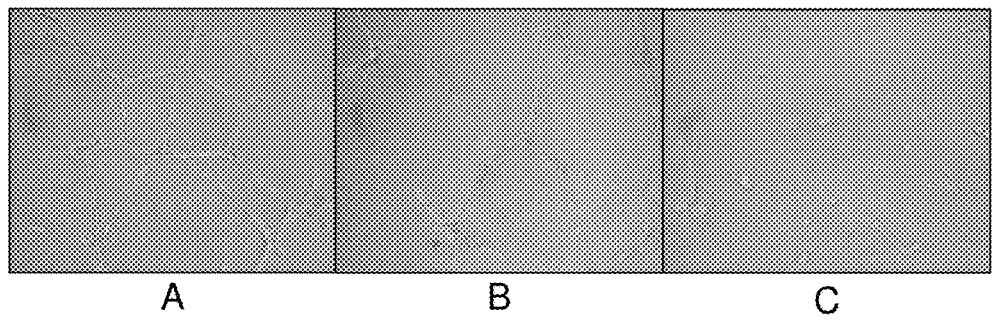
FIG. 1 shows human endothelial cells (HUVEC) photographed at 10× magnification. A shows vascular development caused by treatment with angiogenin (100 ng/ml), B shows positive control VEGF (10 ng/ml) and C is the negative control.
Figure 2:
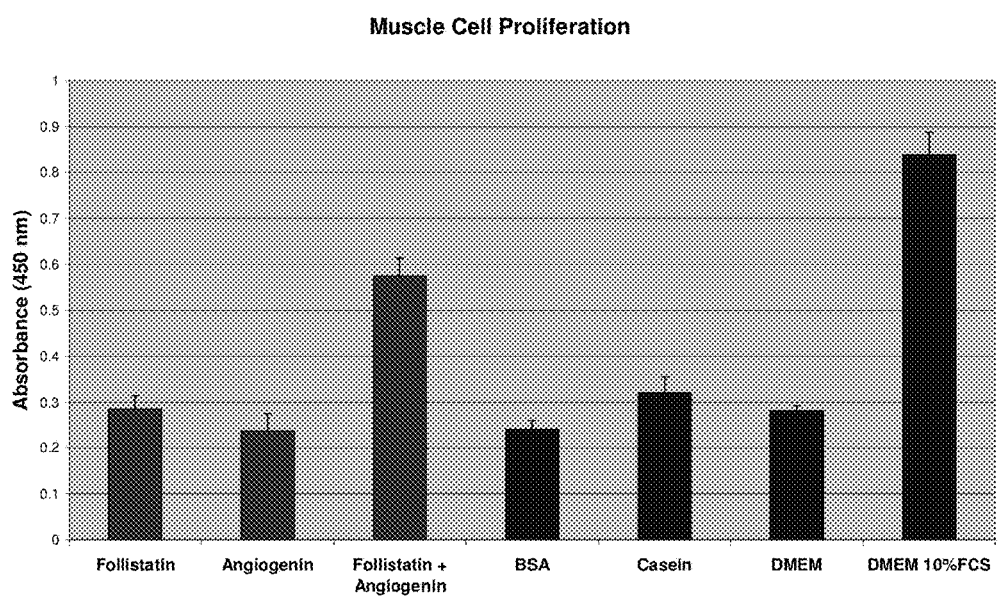
FIG. 2 shows a bar graph illustrating growth of murine C2C12 myoblasts in vitro when administered casein, BSA, follistatin, angiogenin, or follistatin+angiogenin or a positive control (DMEM and 10% FCS).

Angiogenin is a 14 kDa, non-glycosylated polypeptide which is produced by several growing cell types including vascular endothelial cells, aortic smooth muscle cells, fibroblasts, and some tumours such as colon carcinomas, ovarian carcinomas, and breast cancers. Angiogenin has been isolated from a number of sources including normal human plasma, bovine plasma, bovine milk, and mouse, rabbit and pig sera.

Angiogenin is homologous to pancreatic ribonuclease and has distinct ribonucleolytic activity. The protein is able to induce new blood vessel growth; however, it has not been established what role the ribonucleolytic activity of angiogenin plays in angiogenesis induced by this protein.

As well as a potent stimulator of angiogenesis, angiogenin has been shown to possess a number of other activities. However there is no previous disclosure of angiogenin's effect on muscle other than via increasing angiogenesis.

The inventors have shown that angiogenin rich purifications derived by cation-exchange chromatography of milk fractions also contain follistatin, a protein of significantly different charge properties to angiogenin (data not shown). In the prior art, angiogenin and follistatin have been shown to bind to each other in a yeast two-hybrid model. The inventors show for the first time a biologically significant interaction between angiogenin and follistatin in mammalian cells. Follistatin is known as an antagonist of myostatin, a protein said to control muscle growth and development.

The invention in one aspect relates to the treatment of disorders. The terms "treating" and "treatment" as used herein refer to reduction in severity and/or frequency of symptoms, elimination of symptoms and/or underlying cause, prevention of the occurrence of symptoms (prophylaxis) and/or their underlying cause, and improvement or remediation of damage. Thus, for example, the present method of "treating" a disorder encompasses both prevention of the disorder in a predisposed individual and treatment of the disorder in a clinically symptomatic individual.

"Treating" as used herein covers any treatment of, or prevention of a condition in a vertebrate, a mammal, particularly a human, and includes: inhibiting the condition, i.e., arresting its development; or relieving or ameliorating the effects of the condition, i.e., cause regression of the effects of the condition.

"Prophylaxis" or "prophylactic" or "preventative" therapy as used herein includes preventing the condition from occurring or ameliorating the subsequent progression of the condition in a subject that may be predisposed to the condition, but has not yet been diagnosed as having it.

In the prior art myostatin is said to play a role in muscle development and a number of related disorders or diseases. In adults, myostatin mRNA is primarily detected in skeletal muscle although lower concentrations are also found in adipose tissue and cardiac tissue. Myostatin knockout mice have two- to three-fold greater muscle mass than their wild type littermates. The increased muscle mass is the result of fibre hypertrophy and hyperplasia. In addition, the myostatin knockout mice accumulate less fat than their wild type littermates but otherwise appear normal and healthy. Myostatin has also been recently shown to be an important regulator of adipogenesis. Additionally, bone structure and content has been recently studied in myostatin deficient mice.

Since the inventors propose that myostatin actually antagonises the effect of angiogenin on the muscle, they propose that angiogenin can be used to treat any disease in which inhibition of myostatin has previously been suggested.

Accordingly angiogenin may be used in accordance with the present invention to increase muscle mass, increase bone density, decrease muscle wasting, or may be useful for the treatment or prevention of conditions wherein the presence of myostatin causes or contributes to undesirable pathological effects or decrease of myostatin levels has a therapeutic benefit in mammals, preferably humans. In addition, angiogenin may be used to treat conditions where myostatin is not dysregulated, but improved follistatin mediated cell stimulation can be gained by addition of exogenous angiogenin.

Angiogenin can be used to reduce the severity of a pathologic condition, which is characterized, at least in part, by an abnormal amount, development or metabolic activity of muscle or adipose tissue in a subject. It can be administered to prevent, ameliorate or reduce the severity of a wasting disorder, such as cachexia, anorexia, AIDS wasting syndrome, muscular dystrophies, neuromuscular diseases, motor neuron diseases, diseases of the neuromuscular junction, and inflammatory myopathies.

The term "disorder associated with myostatin" refers to disorders of muscle, bone, or glucose homeostasis, and include disorders associated with abnormal myostatin.

The invention extends to treatment of muscular disorders and of diseases associated with muscular degeneration characteristics. Non limiting examples of such disorders are various neuromuscular diseases, cardiac insufficiency, weakness of single muscles such as e.g. the constrictor or bladder muscle, hypo- or hypertension caused by problems with the constrictor function of vascular smooth muscle cells, impotence/erectile dysfunction, incontinence, AIDS-related muscular weakness, and general and age-related amyotrophia.

Disorders of muscle as referred to herein particularly include muscle wasting conditions or disorders in which muscle wasting is one of the primary symptoms.

A muscle is a tissue of the body that primarily functions as a source of power. There are three types of muscles in the body: a) skeletal muscle—striated muscle responsible for generating force that is transferred to the skeleton to enable movement, maintenance of posture and breathing; b) cardiac muscle—the heart muscle; and c) smooth muscle—the muscle that is in the walls of arteries and bowel. The methods of the invention are particularly applicable to skeletal muscle but may have some effect on cardiac and or smooth muscle.

Skeletal muscle fibers are generally classified as type I (oxidative/slow) or type II (glycolytic/fast) fibers. They display marked differences in respect to concentration, metabolism, and susceptibility to fatigue. Type I fibers are mitochondria-rich and mainly use oxidative metabolism for energy production, which provides a stable and long-lasting supply of ATP, and thus are fatigue-resistant. Type II fibers comprise three sub-types: IIa, IIx, and IIb. Type IIb fibers have the lowest levels of mitochondrial content and oxidative enzymes, rely on glycolytic metabolism as major energy source, and are susceptible to fatigue, while the oxidative and contraction functions of type IIa and IIx lie between type I and IIb. Adult skeletal muscle shows plasticity and can undergo conversion between different fiber types in response to exercise training or modulation of motoneuron activity.

Determination of the muscle fiber composition in athletes revealed that elite endurance athletes have relatively more type I fibers than type II fibers in the trained musculature. Marathon runners also tend to have more type I fibers. It was suggested that type I fiber might be a factor governing physical endurance capacity.

On the contrary, ageing and physical inactivity are conditions associated with a decrease in type I fibers, oxidative capacity and insulin sensitivity. It appears that the muscle oxidative capacity is a crucial factor for determining endurance and fatigue resistance. There seem to be an adaptive metabolic response of skeletal muscle to endurance exercise by controlling the number of oxidative muscle fibers (type I fibers).

The conversion of skeletal muscle fiber type IIb to type IIa and type I is regulated by different signalling pathways. For example the Ras/mitogen-activated protein kinase (MAPK), calcineurin, calcium/calmodulin-dependent protein kinase FV and the peroxisome proliferator y coactivator 1 (PGC-I). Angiogenin may modulate these pathways and such may have an influence on the skeletal muscle fibers.

"Muscle wasting" refers to the progressive loss of muscle mass and/or to the progressive weakening and degeneration of muscles, including the skeletal or voluntary muscles which control movement, cardiac muscles which control the heart, and smooth muscles. In one embodiment, the muscle wasting condition or disorder is a chronic muscle wasting condition or disorder. "Chronic muscle wasting" is defined herein as the chronic (i.e. persisting over a long period of time) progressive loss of muscle mass and/or to the chronic progressive weakening and degeneration of muscle.

The loss of muscle mass that occurs during muscle wasting can be characterized by a muscle protein breakdown or degradation, by muscle protein catabolism. Protein catabolism occurs because of an unusually high rate of protein degradation, an unusually low rate of protein synthesis, or a combination of both. Protein catabolism or depletion, whether caused by a high degree of protein degradation or a low degree of protein synthesis, leads to a decrease in muscle mass and to muscle wasting. The term "catabolism" has its commonly known meaning in the art, specifically an energy burning form of metabolism.

Muscle wasting can occur as a result of a pathology, disease, condition or disorder. In one embodiment, the pathology, illness, disease or condition is chronic. In another embodiment, the pathology, illness, disease or condition is genetic. In another embodiment, the pathology, illness, disease or condition is neurological. In another embodiment, the pathology, illness, disease or condition is infectious. As described herein, the pathologies, diseases, conditions or disorders for which the compounds and compositions of the present invention are administered are those that directly or indirectly produce a wasting (i.e. loss) of muscle mass, that is a muscle wasting disorder.

Especially preferred is the treatment of neuromuscular diseases which are aligned with joint or skeletal deformities. In one embodiment, muscle wasting in a subject is a result of the subject having a muscular dystrophy; muscle atrophy; or X-linked spinal-bulbar muscular atrophy (SBMA).

The muscular dystrophies are genetic diseases characterized by progressive weakness and degeneration of the skeletal or voluntary muscles that control movement. The muscles of the heart and some other involuntary muscles are also affected in some forms of muscular dystrophy. The major forms of muscular dystrophy (MD) are: duchenne muscular dystrophy, myotonic dystrophy, becker muscular dystrophy, limb-girdle muscular dystrophy, facioscapulhumeral muscular dystrophy, congenital muscular dystrophy, oculopharyngeal muscular dystrophy, distal muscular dystrophy and emery-dreifuss muscular dystrophy.

Muscular dystrophy can affect people of all ages. Although some forms first become apparent in infancy or childhood, others may not appear until middle age or later. Duchenne MD is the most common form, typically affecting children. Myotonic dystrophy is the most common of these diseases in adults.

Muscle atrophy (MA) is characterized by wasting away or diminution of muscle and a decrease in muscle mass. For example, Post-Polio MA is a muscle wasting that occurs as part of the post-polio syndrome (PPS). The atrophy includes weakness, muscle fatigue, and pain.

Another type of MA is X-linked spinal-bulbar muscular atrophy (SBMA—also known as Kennedy's Disease). This disease arises from a defect in the androgen receptor gene on the X chromosome, affects only males, and its onset is in adulthood.

Sarcopenia is a debilitating disease that afflicts the elderly and chronically ill patients and is characterized by loss of muscle mass and function. Further, increased lean body mass is associated with decreased morbidity and mortality for certain muscle-wasting disorders. In addition, other circumstances and conditions are linked to, and can cause muscle wasting disorders. For example, studies have shown that in severe cases of chronic lower back pain, there is paraspinal muscle wasting.

Muscle wasting and other tissue wasting is also associated with advanced age. It is believed that general weakness in old age is due to muscle wasting. As the body ages, an increasing proportion of skeletal muscle is replaced by fibrous tissue. The result is a significant reduction in muscle power, performance and endurance.

Long term hospitalization due to illness or injury, or disuse deconditioning that occurs, for example, when a limb is immobilized, can also lead to muscle wasting, or wasting of other tissue. Studies have shown that in patients suffering injuries, chronic illnesses, burns, trauma or cancer, who are hospitalized for long periods of time, there is a long-lasting unilateral muscle wasting, and a decrease in body mass.

Injuries or damage to the central nervous system (CNS) are also associated with muscle wasting and other wasting disorders. Injuries or damage to the CNS can be, for example, caused by diseases, trauma or chemicals. Examples are central nerve injury or damage, peripheral nerve injury or damage and spinal cord injury or damage. In one embodiment CNS damage or injury comprise Alzheimer's diseases (AD); stroke, anger (mood); anorexia, anorexia nervosa, anorexia associated with aging and/or assertiveness (mood).

In another embodiment, muscle wasting or other tissue wasting may be a result of alcoholism.

In one embodiment, the wasting disease, disorder or condition being treated is associated with chronic illness This embodiment is directed to treating, in some embodiments, any wasting disorder, which may be reflected in muscle wasting, weight loss, malnutrition, starvation, or any wasting or loss of functioning due to a loss of tissue mass.

In some embodiments, wasting diseases or disorders, such as cachexia; malnutrition, tuberculosis, leprosy, diabetes, renal disease, chronic obstructive pulmonary disease (COPD), cancer, end stage renal failure, sarcopenia, emphysema, osteomalacia, or cardiomyopathy, may be treated by the methods of this invention In some embodiments, wasting is due to infection with enterovirus, Epstein-Barr virus, herpes zoster, HIV, trypanosomes, influenze, coxsackie, rickettsia, trichinella, schistosoma or mycobacteria.

Cachexia is weakness and a loss of weight caused by a disease or as a side effect of illness. Cardiac cachexia, i.e. a muscle protein wasting of both the cardiac and skeletal muscle, is a characteristic of congestive heart failure. Cancer cachexia is a syndrome that occurs in patients with solid tumors and hematological malignancies and is manifested by weight loss with massive depletion of both adipose tissue and lean muscle mass.

Cachexia is also seen in acquired immunodeficiency syndrome (AIDS), human immunodeficiency virus (HIV)-associated myopathy and/or muscle weakness/wasting is a relatively common clinical manifestation of AIDS. Individuals with HIV-associated myopathy or muscle weakness or wasting typically experience significant weight loss, generalized or proximal muscle weakness, tenderness, and muscle atrophy.

Untreated muscle wasting disorders can have serious health consequences. The changes that occur during muscle wasting can lead to a weakened physical state resulting in poor performance of the body and detrimental health effects.

Thus, muscle atrophy can seriously limit the rehabilitation of patients after immobilizations. Muscle wasting due to chronic diseases can lead to premature loss of mobility and increase the risk of disease-related morbidity. Muscle wasting due to disuse is an especially serious problem in elderly, who may already suffer from age-related deficits in muscle function and mass, leading to permanent disability and premature death as well as increased bone fracture rate. Despite the clinical importance of the condition few treatments exist to prevent or reverse the condition. The inventors propose that angiogenin can be used to prevent and treat muscle wasting or atrophy associated with any of the conditions recited above.

Angiogenin, particularly in combination with follistatin or when administered orally is shown herein to be neuroprotective and hence find utility in treating neurological disorders or diseases affecting the nervous system, particularly motor neurone diseases. Exemplary motor neuron diseases that can be treated with angiogenin include Amyotrophic Lateral Sclerosis (ALS) (also known as Lou Gehrig's Disease), Infantile Progressive Spinal Muscular Atrophy (SMA, SMA1 or WH) (also known as SMA Type 1, Werdnig-Hoffman), Intermediate Spinal Muscular Atrophy (SMA or SMA2) (also known as SMA Type 2), Juvenile Spinal Muscular Atrophy (SMA, SMA3 or KW) (also known as SMA Type 3, Kugelberg-Welander), Spinal Bulbar Muscular Atrophy (SBMA) (also known as Kennedy's Disease and X-Linked SBMA), and Adult Spinal Muscular Atrophy (SMA).

Exemplary inflammatory myopathies that can be treated with angiogenin include Dermatomyositis (PM/DM), Polymyositis (PM/DM), and Inclusion Body Myositis (IBM).

Exemplary diseases of the neuromuscular junction that can be treated with angiogenin include: Myasthenia Gravis (MG), Lambert-Eaton Syndrome (LES), and Congenital Myasthenic Syndrome (CMS).

Exemplary myopathies due to endocrine abnormalities that can be treated with angiogenin include Hyperthyroid Myopathy (HYPTM) and Hypothyroid Myopathy (HYPOTM).

Exemplary diseases of peripheral nerve that can be treated with angiogenin include Charcot-Marie-Tooth Disease (CMT), Dejerine-Sottas Disease (DS), and Friedreich's Ataxia (FA).

Other exemplary myopathies that can be treated with angiogenin include Myotonia Congenita (MC), Paramyotonia Congenita (PC), Central Core Disease (CCD), Nemaline Myopathy (NM), Myotubular Myopathy (MTM or MM), and Periodic Paralysis (PP).

Angiogenin can also be used to promote wound healing and to treat wounds, both of which uses have previously been proposed for myostatin inhibitors.

Exemplary metabolic diseases of muscle that can be treated with angiogenin include Phosphorylase Deficiency (MPD or PYGM), Acid Maltase Deficiency (AMD), Phosphofructokinase Deficiency (PFKM), Debrancher Enzyme Deficiency (DBD), Mitochondrial Myopathy (MITO), Carnitine Deficiency (CD), Carnitine Palmityl Transferase Deficiency (CPT), Phosphoglycerate Kinase Deficiency (PGK), Phosphoglycerate Mutase Deficiency (PGAM or PGAMM), Lactate Dehydrogenase Deficiency (LDHA), and Myoadenylate Deaminase Deficiency (MAD). These diseases have previously been proposed to be treated by myostatin inhibitors.

In the accompanying experiments the inventors show that angiogenin reduces fat. This has previously been shown for myostatin inhibitors and shows that angiogenin can be used to treat disease connected to impaired lipid metabolism such as dyslipidemia and related lipid abnormalities such as hyperlipidemia, hypercholesteremia, hypertriglyceridemia and mixed dyslipidemia.

Dyslipidemia is characterized by abnormalities in circulating lipid levels due to alterations in lipid metabolism. These abnormalities can include any one or several of the different circulating lipid fractions (cholesterol, triglyceride, lipoprotein). Dyslipidemia includes hypercholesterolemia, which is an elevation of serum cholesterol above the normal limit (normal safe limit is approximately in the range of 125-200 mg/dl in human blood), hypertriglyceridemia which is an increase of serum triglycerides above the normal level (normal safe limit is approximately in the range of 30-140 mg/dl in human blood) and mixed lipid disorders.

Dyslipidemia includes hypertriglyceridemia and mixed dyslipidemia (hyperlipidemia). Hypertriglyceridemia involves a rise in the levels of very low density lipoprotein (VLDL), while mixed dyslipidemia (hyperlipidemia) involves a combination both hypertriglyceridemia and hypercholesterolemia and is also often associated with a drop in high density lipoprotein (HDL) levels. Thus, dyslipidemia is also a disorder of lipoprotein metabolism that results in an overproduction or a deficiency of lipoproteins. Dyslipidemia is typically characterized by any one or more of the following: elevated plasma triglycerides, elevated total plasma cholesterol, low High Density Lipoprotein cholesterol (HDL-c), elevated levels of Low Density Lipoprotein cholesterol (LDL-c). For example, dyslipidemia may be one or more of the following conditions: low HDL-c (<35 or 40 mg/dl), high triglycerides (>200 mg/dl), high LDL-c (>150 mg/dl), elevated cholesterol (>200 mg/dl).

Dyslipidemia is widely considered as one of the main risk factor for cardiovascular vascular diseases (CVD) and atherogenesis. Cardiovascular disorders are among the leading causes of disability and death worldwide. High serum cholesterol, particularly cholesterol associated with LDL and VLDL, is one of the principal risk factors for atherogenesis. High triglycerides, increased small LDL, and decreased HDL levels all appear to be independently atherogenic. There is a strong inverse association between plasma HDL and the risk of CVD. A positive association exists between LDL cholesterol and risk of CVD. Thus, the risk of coronary artery disease increases when LDL and VLDL levels increase while high levels of cholesterol carried in HDL is protective against coronary artery disease. Triglycerides also seem to play an important role in CVD. High level of fasting triglycerides is a strong risk factor for ischaemic heart disease in elderly men independently of other major risk factors including HDL-cholesterol. People with combined hyperlipidemia, which is characterized by elevated serum levels of both cholesterol and triglycerides, run a higher risk of heart disease than those with only a high LDL cholesterol level. Therefore, lowering both levels is a desired goal.

Diseases connected to impaired glucose metabolism and impaired insulin action include diabetes mellitus, especially diabetes mellitus type 1 and 2, more especially (non-autoimmune) non-insulin dependent diabetes mellitus (NIDDM; so called Type 2 Diabetes). Another such disease is syndrome X or metabolic syndrome.

Diabetes mellitus defines a complex of metabolic diseases derived from multiple causative factors and is characterized by impaired glucose metabolism, usually associated with impaired protein and fat metabolism. This results in elevated fasting and postprandial serum glucose that leads to complications if left untreated. Four different forms of diabetes mellitus are known, (1) type 1 diabetes mellitus, (2) type 2 diabetes mellitus, (3) the so-called gestational diabetes mellitus, which begins or is recognized for the first time during pregnancy, and (4) some other forms which are mainly based on genetic defects.

The term "diabetes mellitus" includes, but is not limited to, metabolic abnormalities such as increased blood glucose level, obesity associated pathologies, impaired glucose tolerance, increased insulin resistance, hyperlipidemia, dyslipidemia, increase in cholesterol (hypercholesterinemia, hypertriglycerinemia), hyperinsulinemia, hypertension, and microalbuminuria. Impaired glucose tolerance and impaired fasting glucose are the two symptoms referred to as pre-diabetes mellitus. This stage is associated with the so-called insulin resistance, one of a group of metabolic diseases called "syndrome X" or "metabolic syndrome", particularly associated with a high fat to muscle ratio. Since type 2 diabetes mellitus is often associated with other symptoms from syndrome X, such as hypertriglyceridemia or dyslipidemia, and the use of angiogenin should greatly improve the fat to muscle ratio of a subject the methods of the present invention are also useful for the treatment or prevention of syndrome X.

The two major forms of diabetes mellitus are the type 1 and type 2 diabetes mellitus, of which type 2 diabetes mellitus is the most prevailing form. Type 1 and type 2 diabetes mellitus are associated with hyperglycemia, hypercholesterolemia and hyperlipidemia. The insensitivity to insulin and absolute insulin deficiency in type 1 and 2 diabetes mellitus leads to a decrease in glucose utilization by the liver, muscle and the adipose tissue and to increased blood glucose levels. Uncontrolled hyperglycemia is associated with the dysfunction and failure of various organs such as the eyes, heart, blood vessels, kidney and nerves thus leading to increased and premature mortality due to an increased risk for microvascular and macrovascular diseases, including nephropathy, neuropathy, retinopathy, ulceration of the legs and feet, fatty liver disease, hypertension, cardiovascular diseases, and cerebrovascular diseases (stroke), the so-called diabetic complications.

Recent evidence showed that tight glycemic control is a major factor in the prevention of these complications in both type 1 and type 2 diabetes mellitus. Therefore, optimal glycemic control by drugs or therapeutic regimens is an important approach for the treatment of diabetes mellitus.

Type 1 diabetes mellitus is the form of diabetes mellitus which usually begins with childhood or puberty and is characterized by an auto-immune destruction of the insulin-producing R-cells leading to a complete deficiency of insulin secretion.

Type 2 diabetes mellitus is the form of diabetes mellitus which occurs predominantly in adults in whom adequate production of insulin is available in the early stage of the diseases, yet a defect exists in insulin sensitivity, especially in insulin-mediated utilization and metabolism of glucose in peripheral tissues. The changes in various tissues associated with type 2 diabetes mellitus exist even before clinical symptoms are detected.

Also contemplated is the treatment of insulin resistance induced by trauma (e.g. burns or nitrogen imbalance) and adipose tissue disorders (e.g. obesity).

Other uses for angiogenin in accordance with the invention include for treatment of osteoporosis, especially in the elderly and/or postmenopausal women; glucocorticoid-induced osteoporosis; osteopenia; osteoarthritis; osteoporosis-related fractures; and traumatic or chronic injury to muscle tissue. Further uses for angiogenin include treatment of low bone mass due to chronic glucocorticoid therapy, premature gonadal failure, androgen suppression, vitamin D deficiency, secondary hyperparathyroidism, nutritional deficiencies, and anorexia nervosa.

The invention in other aspects also contemplates treating healthy individuals to cause an increase in muscle mass, strength, function or overall physique. Angiogenin is also proposed to promote muscle recovery from injury or trauma or damage or overuse through training and therefore to increase exercise tolerance.

The term "increase in muscle mass" refers to the presence of a greater amount of muscle after treatment with angiogenin relative to the amount of muscle mass present before the treatment.

The term "increase in muscle strength" refers to the presence of a muscle with greater force generating capacity after treatment with angiogenin relative to that present before the treatment.

The term "increase in muscle function" refers to the presence of muscle with greater variety of function after treatment with angiogenin relative to that present before the treatment.

The term "increase in exercise tolerance" refers to the ability to exercise with less rest between exercise after treatment with angiogenin relative to that needed before the treatment.

A muscle is a tissue of the body that primarily functions as a source of power. There are three types of muscles in the body: a) skeletal muscle—striated muscle responsible for generating force that is transferred to the skeleton to enable movement, maintenance of posture and breathing; b) cardiac muscle—the heart muscle; and c) smooth muscle—the muscle that is in the walls of arteries and bowel. The methods of the invention are particularly applicable to skeletal muscle but may have some effect on cardiac and or smooth muscle. Reference to skeletal muscle as used herein also includes interactions between bone, muscle and tendons and includes muscle fibres and joints.

Whilst angiogenin has previously been suggested to have an effect on cardiac muscle by virtue of its angiogenic activity and ability to provide increased blood flow to a muscle, this effect was restricted to oxidative muscles (type I and type IIa). The follistatin mediated effects of angiogenin on muscle as seen in the present invention are distinct from those relating to angiogenesis as evidenced by all muscle fibres being affected.

The term "decrease in fat" refers to the presence of a reduced amount of fat after treatment with angiogenin relative to the amount of fat present before the treatment. The present invention is particularly applicable to visceral fat, fat located inside the peritoneal cavity and around internal organs. It may also effect subcutaneous fat and/or intramuscular fat.

The proposed uses of angiogenin on healthy individuals will be useful to athletes, both elite and amateur, body builders, those desirous of weight loss of enhanced physique and manual workers.

Since angiogenin is highly conserved in sequence and function across species, the methods of the invention are applicable in non-human mammals or avian species [e.g. domestic animals (e.g., canine and feline), sports animals (e.g., equine), food-source animals (e.g., bovine, porcine and ovine), avian species (e.g., chicken, turkey, other game birds or poultry)] wherein the presence of myostatin causes or contributes to undesirable pathological effects or decrease of myostatin levels has a therapeutic benefit.

The angiogenin or angiogenin agonist may be provided as a pharmaceutical, veterinary or neutraceutical composition or as a food.

A pharmaceutical composition is one which is suitable for administration to humans. A veterinary composition is one that is suitable for administration to animals. Generally such compositions will contain purified angiogenin or angiogenin agonist or at the very least all components of the composition will be verifiable.

The compositions used in the methods of the first to eleventh aspects may comprise one or more carriers and optionally other therapeutic agents. Each carrier, diluent, adjuvant and/or excipient may be pharmaceutically "acceptable".

By "pharmaceutically acceptable carrier" is meant a material which is not biologically or otherwise undesirable, i.e., the material may be administered to an individual along with the selected active agent without causing any undesirable biological effects or interacting in a deleterious manner with any of the other components of the pharmaceutical composition in which it is contained. Similarly, a "pharmaceutically acceptable" salt or ester of a novel compound as provided herein is a salt or ester which is not biologically or otherwise undesirable.

As used herein, a "pharmaceutical carrier" is a pharmaceutically acceptable solvent, suspending agent or vehicle for delivering the agent to the subject. The carrier may be liquid or solid and is selected with the planned manner of administration in mind. Each carrier must be pharmaceutically "acceptable" in the sense of being not biologically or otherwise undesirable i.e. the carrier may be administered to a subject along with the agent without causing any or a substantial adverse reaction.

The composition may be administered orally, topically, or parenterally in formulations containing conventional non-toxic pharmaceutically acceptable carriers, adjuvants, and vehicles.

The term parenteral as used herein includes intravenous, intraarterial, intraperitoneal, intramuscular, subcutaneous, subconjunctival, intracavity, transdermal and subcutaneous injection, aerosol for administration to lungs or nasal cavity or administration by infusion by, for example, osmotic pump.

The composition may be administered orally as tablets, aqueous or oily suspensions, lozenges, troches, powders, granules, emulsions, capsules, syrups or elixirs. The composition for oral use may contain one or more agents selected from the group of sweetening agents, flavouring agents, colouring agents and preserving agents in order to produce pharmaceutically elegant and palatable preparations. Suitable sweeteners include sucrose, lactose, glucose, aspartame or saccharin. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable preservatives include sodium benzoate, vitamin E, alphatocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate. The tablets may contain the agent in admixture with non-toxic pharmaceutically acceptable excipients which are suitable for the manufacture of tablets.

These excipients may be, for example, (1) inert diluents, such as calcium carbonate, lactose, calcium phosphate or sodium phosphate; (2) granulating and disintegrating agents, such as corn starch or alginic acid; (3) binding agents, such as starch, gelatin or acacia; and (4) lubricating agents, such as magnesium stearate, stearic acid or talc. These tablets may be uncoated or coated by known techniques to delay disintegration and absorption in the gastrointestinal tract and thereby provide a sustained action over a longer period. For example, a time delay material such as glyceryl monostearate or glyceryl distearate may be employed.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, anti-microbials, anti-oxidants, chelating agents, growth factors and inert gases and the like.

The compositions may also contain other active compounds providing supplemental, additional, or enhanced therapeutic functions. The pharmaceutical compositions may also be included in a container, pack, or dispenser together with instructions for administration.

Other therapeutically useful agents, such as growth factors (e. g., BMPs, TGF-P, FGF, IGF), cytokines (e. g., interleukins and CDFs), antibiotics, and any other therapeutic agent beneficial for the condition being treated may optionally be included in or administered simultaneously or sequentially with the angiogenin or angiogenin agonist.

Angiogenin or its agonists may also be presented for use in the form of veterinary compositions, which may be prepared, for example, by methods that are conventional in the art. Examples of such veterinary compositions include those adapted for:

(a) oral administration, external application, for example drenches (e.g. aqueous or non-aqueous solutions or suspensions); tablets or boluses; powders, granules or pellets for admixture with feed stuffs; pastes for application to the tongue, particularly adapted for protection through the rumen if to be administered to ruminants;

(b) parenteral administration for example by subcutaneous, intramuscular or intravenous injection, e.g. as a sterile solution or suspension; or (when appropriate) by intramammary injection where a suspension or solution is introduced in the udder via the teat;

(c) topical applications, e.g. as a cream, ointment or spray applied to the skin; or (d) intravaginally, e.g. as a pessary, cream or foam.

It is especially advantageous to formulate the compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Compositions comprising angiogenin or an agonist thereof are to be administered in therapeutically effective amounts. As used herein, an "effective amount" of angiogenin is a dosage which is sufficient to reduce the activity of myostatin to achieve a desired biological outcome. The desired biological outcome may be any therapeutic benefit including an increase in muscle mass, an increase in muscle strength, improved metabolism, decreased adiposity, or improved glucose homeostasis. Such improvements may be measured by a variety of methods including those that measure lean and fat body mass (such as duel ray scanning analysis), muscle strength, serum lipids, serum leptin, serum glucose, glycated hemoglobin, glucose tolerance, and improvement in the secondary complications of diabetes.

Generally, a therapeutical effective amount may vary with the subject's age, condition, and sex, as well as the severity of the medical condition in the subject. The dosage may be determined by an physician and adjusted, as necessary, to suit observed effects of the treatment. Appropriate dosages for administering angiogenin or its agonists may range from 5 mg to 100 mg, from 15 mg to 85 mg, from 30 mg to 70 mg, or from 40 mg to 60 mg. The compositions can be administered in one dose, or at intervals such as once daily, once weekly, and once monthly.

Dosage schedules can be adjusted depending on the half life of angiogenin or its agonist, or the severity of the patient's condition.

Generally, the compositions are administered as a bolus dose, to maximize the circulating levels of angiogenin for the greatest length of time after the dose. Continuous infusion may also be used after the bolus dose.

It is also contemplated that the methods utilise a neutraceutical composition to provide the angiogenin. A neutraceutical composition for use in the methods is provided.

The term "nutraceutical" as used herein refers to an edible product isolated or purified from food, in this case from a milk product, which is demonstrated to have a physiological benefit or to provide protection or attenuation of an acute or chronic disease or injury when orally administered. The nutraceutical may thus be presented in the form of a dietary preparation or supplement, either alone or admixed with edible foods or drinks.

The nutraceutical composition may be in the form of a soluble powder, a liquid or a ready-to-drink formulation. Alternatively, the nutritional composition may be in solid form as a food; for example in the form of a ready-to-eat bar or breakfast cereal. Various flavours, fibres, sweeteners, and other additives may also be present.

The nutraceutical preferably has acceptable sensory properties (such as acceptable smell, taste and palatability), and may further comprise vitamins and/or minerals selected from at least one of vitamins A, B1, B2, B3, B5, B6, B11, B12, biotin, C, D, E, H and K and calcium, magnesium, potassium, zinc and iron.

The nutraceutical composition may be produced as is conventional; for example, the composition may be prepared by blending together the protein and other additives. If used, an emulsifier may be included in the blend. Additional vitamins and minerals may be added at this point but are usually added later to avoid thermal degradation.

If it is desired to produce a powdered nutraceutical composition, the protein may be admixed with additional components in powdered form. The powder should have a moisture content of less than about 5% by weight. Water, preferably water which has been subjected to reverse osmosis, may then be mixed in to form a liquid mixture.

If the nutraceutical composition is to be provided in a ready to consume liquid form, it may be heated in order to reduce the bacterial load. If it is desired to produce a liquid nutraceutical composition, the liquid mixture is preferably aseptically filled into suitable containers. Aseptic filling of the containers may be carried out using techniques commonly available in the art. Suitable apparatus for carrying out aseptic filling of this nature is commercially available.

Preferably the neutraceutical composition also comprises one or more pharmaceutically acceptable carriers, diluents or excipients. Neutraceutical compositions may comprise buffers such as neutral buffered saline, phosphate buffered saline and the like; carbohydrates such as glucose, mannose, sucrose or dextrans; mannitol; proteins; polypeptides or amino acids such as glycine; antioxidants; chelating agents such as EDTA; adjuvants and preservatives.

The neutraceutical may be an infant formula, particularly a humanised milk formula for administration to infants. Such an infant formula may find utility in treating failure to thrive or premature or low birth weight babies. It may also be administered to infants or children to improve cognitive function.

The angiogenin used in the methods of the invention may be from any source. It may be natural, synthetic or recombinant in origin. Recombinant angiogenin can be based on the angiogenin sequence from any species, including humans, cows, sheep, mouse, etc. Recombinant human angiogenin is available from R & D Systems.

Angiogenin is known to be present in normal human plasma, bovine plasma, bovine milk, bovine plasma and mouse, rabbit and pig sera. The DNA and protein sequences of at least human angiogenin are available and recombinant human angiogenin is available commercially from Abnova Corporation (Taiwan) for small scale applications.

In one embodiment the angiogenin is prepared from plasma or milk from livestock animals as readily available sources of angiogenin on a commercial scale.

The milk may be obtained from any lactating animal, e.g. ruminants such as cows, sheep, buffalos, goats, and deer, non-ruminants including primates such as a human, and monogastrics such as pigs. In a preferred embodiment the angiogenin is extracted from cow's milk. The animal from which angiogenin is produced may be a transgenic animal designed to over-express angiogenin in its milk.

The inventors of the present application have shown that in bovine milk, angiogenin is present in the highest or most concentrated amount (up to 12 mg/litre) within the first 1 to 14 days of lactation. Following this, the concentration falls to a base level of approximately 1 to 2 mg/litre. Therefore it is preferred that cow's milk which obtained within the first 14 days of lactation as a source of angiogenin for use in the methods of the first to eleventh aspects. Given the residual angiogenin levels in cow's milk from later lactation, it may still be used a source for the methods of the invention.

The angiogenin used in the methods of the invention may be isolated or purified. Purified or isolated angiogenin is substantially free of at least one agent or compound with which it is naturally associated. For instance, an isolated protein is substantially free of at least some cellular material or contaminating protein from the cell or tissue source from which it is derived. The phrase "substantially free of cellular material" refers to preparations where the angiogenin is at least 50 to 59% (w/w) pure, at least 60 to 69% (w/w) pure, at least 70 to 79% (w/w) pure, at least 80-89% (w/w) pure, at least 90-95% pure, or at least 96%, 97%, 98%, 99% or 100% (w/w) pure.

Recombinant angiogenin preparations in bacteria may be used as a source of angiogenin and may be provided in the form of protein aggregates.

As bovine milk is a natural product that has been in food chain for hundreds of years, the angiogenin used as a nutraceutical need not be totally pure. However, to reduce the amount of composition to be administered it is preferred that the angiogenin is concentrated significantly with respect to its concentration in milk. Preferably the angiogenin is administered in at a concentration of at least 10 times its concentration in milk and more preferably 20, 30, 40, or 50 times its concentration in milk.

When provided as a food the angiogenin can take the form of a food supplement, a nutritional formulation, a sports nutrition supplement or an infant formula.

Persons skilled in the art will appreciate that variants of bovine angiogenin exist in nature and can be manufactured. Use of such variants is contemplated by the present invention.

One of skill in the art will recognize that angiogenin may contain any number of conservative changes its amino acid sequence without altering its biological properties. Such conservative amino acid modifications are based on the relative similarity of the amino acid side-chain substituents, for example, their hydrophobicity, hydrophilicity, charge, size, and the like. Exemplary conservative substitutions which take various of the foregoing characteristics into consideration are well known to those of skill in the art and include arginine and lysine; glutamate and aspartate; serine and threonine; glutamine and asparagine; and valine, leucine, and isoleucine.

The present invention also includes the use of variants, homologues, and fragments of angiogenin. For example, the nucleic or amino acid sequence for angiogenin may comprise a sequence at least 70% to 79% identical to the nucleic or amino acid sequence of the native protein, or at least 80% to 89% identical, or at least 90% to 95% identical, or at least 96% to 100% identical.

Persons skilled in the art would really appreciate the numerous software packages to enable them to design or homologues of the angiogenin nucleotide and amino acid sequences, for example the "BLAST" program or other suitable packages.

It is understood by one of ordinary skill in the art that certain amino acids may be substituted for other amino acids in a protein structure without adversely affecting the activity of angiogenin. It is thus contemplated by the inventors that various changes may be made in the amino acid sequences of angiogenin without appreciable loss of their biological utility or activity. Such changes may include deletions, insertions, truncations, substitutions, fusions, shuffling of motif sequences, and the like.

In addition the angiogenin may be modified, for example by glycosylation, by conjugation to a polymer to increase their circulating half-life, by pegylation or other chemical modification. Such modified proteins are also envisaged for use in the method of the present invention.

Persons skilled in the art will appreciate that the angiogenin used may be modified to improve storage stability, bioactivity, circulating half life, or for any other purpose using methods available in the art. For example it may be desirable to introduce modification to improve storage stability. However, as angiogenin is particularly resistant to degradation such modification may not be essential.

The invention refers to agonists of angiogenin. An agonist is a compound that is capable of directly or indirectly having an effect through the receptor activated by angiogenin. Preferably angiogenin agonists act through the angiogenin receptor and preferably bind the receptor. Persons skilled in the art will appreciate how to design agonists of angiogenin. Suitable agonists include angiogenin agonist antibodies and mimetic compounds.

Angiogenin, its agonists and variants may be used in the manufacture of a medicament for use in the methods of the invention.

In a preferred embodiment of the methods and uses of the invention angiogenin is administered orally, particularly in the form of an angiogenin enriched extract from milk or plasma or in the form of recombinant angiogenin Particularly the orally administered angiogenin is prepared from cow's milk or a fraction thereof, for example using the process described in example 1. Such fraction has been found to provide angiogenin able to act systemically, without substantial degradation in the gut. Such fraction is able to be provided orally without employing carriers or other mechanisms to enhance the bioavailability of angiogenin.

Angiogenin administered in accordance with the methods of the first to eleventh aspects is anticipated to interact with endogenous follistatin (if recombinant angiogenin is used) or the enriched angiogenin extract may also contain follistatin. Administration of angiogenin plus follistatin (either simultaneously or sequentially in any order) is shown herein to have a more than additive effect and accordingly a composition comprising angiogenin and follistatin is provided, as well as each of the methods of treatment contemplating administration of follistatin with angiogenin. It is particularly important to co-administer (either simultaneously or sequentially) follistatin with angiogenin in situations where an individual is follistatin deficient. As follistatin levels decrease with age, co-administration of follistatin with angiogenin is particularly contemplated when treating the elderly.

In a co-administration regime, angiogenin may be administered orally and follistatin administered orally or otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

It must also be noted that, as used in the subject specification, the singular forms "a", "an" and "the" include plural aspects unless the context clearly dictates otherwise.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

The invention is now further described in detail by reference to the following example. The example is provided for purposes of illustration only, and is not intended to be limiting unless otherwise specified. Thus, the invention encompasses any and all variations which become evident as a result of the teaching provided herein.

Example 1: Process for the Preparation of an Angiogenin-Enriched Fraction from Skim Milk A 10 cm deep column was packed with SP Sepharose Big Beads (GE Healthcare) such that the total bed volume of the column was 29.7 litres. To the column a flow of skimmed cow's milk was applied at a linear flow rate of 331 cm/h (34 litres of skimmed milk per litre of resin per hour) for 2 hours until the volume of skimmed milk applied was 68 times the volume of the resin packed into the column.

The milk remaining in the column was removed by adding 2.5 column volumes (CV) of water at a linear flow rate of 147 cm/h (15 litres of buffer per litre of resin per hour), or 0.25 CV/min, for 10 min.

The angiogenin-depleted lactoperoxidase fraction was eluted from the column with 2.5 CV of a buffer containing sodium ions equivalent to 2.0% (0.34M) NaCl, at pH 6.5, by flowing the cation buffer solution at a linear flow rate of 75 cm/h (7.5 litres of cation buffer solution per litre of resin per hour), or 0.125 CV/min, for 20 min. The first 0.5 litres of cation buffer solution per litre of resin was discarded to drain and the next 2.5 litres of cation buffer solution per litre of resin was collected as the angiogenin-depleted lactoperoxidase fraction (including 0.5 litres of cation buffer solution per litre of resin overlapping the application time of the next buffer, i.e. breakthrough time).

The angiogenin-enriched fraction was then eluted from the column with 2.5 CV of a buffer containing sodium ions equivalent to 2.5% w/v (0.43M) NaCl, at pH 6.5, by flowing the cation buffer solution at a linear flow rate of 75 cm/h (7.5 litres of cation buffer solution per litre of resin per hour), or 0.125 CV/min, for 20 min. The first 0.5 litres of cation buffer solution per litre of resin was discarded to drain and the next 2.5 litres of cation buffer solution per litre of resin was collected as the angiogenin-enriched fraction (including 0.5 litres of cation buffer solution per litre of resin overlapping the application time of the next buffer).

Finally, the lactoferrin fraction was eluted from the column with 2.5 CV of a buffer containing sodium ions equivalent to 8.75% w/v (1.5M) NaCl, at pH 6.5, by flowing the cation buffer solution at a linear flow rate of 75 cm/h (7.5 litres of cation buffer solution per litre of resin per hour), or 0.125 CV/min, for 20 min. The first 0.5 litres of cation buffer solution per litre of resin was discarded to drain and the next 2.5 litres of cation buffer solution per litre of resin was collected as the lactoferrin fraction.

The angiogenin-enriched fraction that was collected was ultrafiltrated (NMWCO 5 kDa) to concentrate and reduce the salt content. The resultant concentrate was freeze-dried and stored at room temperature for subsequent use.

The angiogenin-enriched fraction was analysed for angiogenin content by SDS-PAGE and the fraction was found to contain 57% (protein basis) of a low molecular weight (14 kDa) protein which was confirmed to be angiogenin by MALDI-TOF/TOF MS (results not shown).

Persons skilled in the art would appreciate that angiogenin from other sources or purified by other means could be used in the methods of the invention. The above example is merely to show how the actual source of angiogenin used in the following experiments was made and is in no way intended to be limiting.

Whilst it may be considered that the angiogenin enriched fraction may contain additional bioactive components which are having an effect, the comparable amount of angiogenin as available in skim milk (concentration 2%) had comparable activity in the examples shown to the angiogenin enriched fraction (data not shown).

Example 2: In Vitro Analysis—Bovine Angiogenin is Active on Human Cells

Angiogenin was provided in an enriched extract prepared from bovine skim-milk according to the method described above.

An angiogenesis assay employing human umbilical vein endothelial cells (HUVECS) was used to determine if bovine angiogenin is active on human cells. HUVEC cells were routinely maintained in Endothelial cell basal (ECB) medium, supplemented with bovine brain extract, EGF, hydrocortisone and 10% FBS (Clonetics). Assays were performed in triplicate in 48 well tissue culture plates. 150 µl of Matrigel (BD biosciences) was first allowed to polymerise on the bottom of each well. HUVEC cells were resuspended in ECB with now 1% FBS and bovine angiogenin, at $0.5 \times 10^6$ cells/ml. The cells ($2.5 \times 10^4$ cells/well) were then plated on to the matrigel matrix and incubated at 37° C. for 24 hours. Human vascular endothelia growth factor (VEGF) 10 ng/ml replaced angiogenin as a positive control and ECB media 1% FBS alone was used a negative control. Vascular development was observed and photographed at 10× magnification and the results shown in FIG. 1.

The results show that bovine angiogenin induces vascular development of HUVEC on matrigel in the same manor as human VEGF and therefore bovine angiogenin is shown to be active on human cells.

Example 3: In Vitro Muscle Cell Growth Assays

Muscle cells (C2C12; mouse myoblasts) were seeded into 96-well plates at a starting density of $1 \times 10^4$ cells/well in Dulbecco's modified Eagle's medium (DMEM) containing 10% fetal bovine serum (FBS). The cells were cultured overnight at 37° C.; 5% $CO_2$. The next day the serum containing media was removed and the cells washed in PBS. The cells were then cultured in 100 µl serum free DMEM supplemented with test agents (n=7) for 48 hrs at 37° C.; 5% $CO_2$. To quantitate the cell growth 10 µl WST-1 cell proliferation reagent (Roche) was added to each to each well and the cells incubated for a further 3 hours at 37° C. During this time viable cells convert the WST-1 reagent to a soluble formazan dye which was measured in a microplate reader, the absorbance at 450 nm directly correlates to the cell number. Stimulation of cell growth by the agents was compared to a positive control (10% FCS) and negative controls (DMEM+vehicle control; DMEM containing BSA or casein at appropriate protein loads).

For muscle cell differentiation studies, C2C12 myoblasts were seeded into the 6 well plates at $25 \times 10^4$ cells in 2 ml of media (DMEM, 10% FBS) and allowed to attach overnight. To induce differentiation into myotubes, the culture media was removed and replaced with DMEM alone or DMEM supplemented with 2% horse serum. The effects of bAngiogenin (0.1 µg/ml-100 µg/ml; 10 µg/ml where not stated), rhAngiogenin (0.1 µg/ml-10 µg/ml; 1 µg/ml where not stated), rhFollistatin (0.1 µg/ml) and rhMyostatin (50 ng/ml) were tested. All recombinant proteins were purchased from RnD Systems. Images of cells were taken and creatine kinase (CK) activity was measured after treatment for 96 hours, or 48 hours for experiments involving myostatin. We measured Creatine Kinase activity activated by N-Acetyl Cysteine (NAC) according to the manufacture's instructions. Briefly for each assay a fresh vial of CK-NAC reagent (Thermo Cat #TR14010) with made up with 10 ml of sterile water. 17.51 of each sample was then mixed with 350 µl CK-NAC reagent and triplicate 100µl aliquots assayed in 96 well plates. The absorbance at 340 nm was then measured for five minutes. CK activity was calculated from the change in abs/min using the following equations:

$$\text{Activity } (U/L) = \Delta\text{abs min} - 1 \times \text{Factor}$$

$$\text{Factor} = \frac{\text{Total vol} \times 1000}{6.3 \times \text{sample vol} \times \text{cuvette pathlength}}$$

$$= 0.1 \times 1000 / (6.3 \times .005 \times 1)$$

$$= 3174.6$$

$$CK \text{ Activity } (U/L) = \Delta\text{abs min} - 1 \times 3174.6$$

For microarray analyses of cell cultures, total RNA was extracted from cultured cells using the RNeasy mini RNA isolation kit (Qiagen) and quantitated by measuring absorbance at 260 nm with the Nanodrop 1000 spectrophotometer. Purity was also assessed by obtaining 260 nm/280 nm and 260 nm/230 nm ratios. RNA integrity was assessed by running a sample of each RNA on the Bioanalyser 2100 using the RNA 6000 Nano LabChip kit (Agilent).

Figure 3:
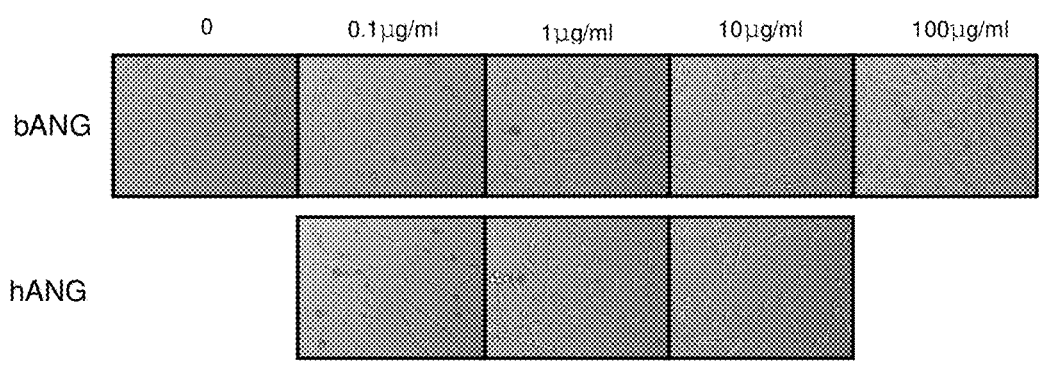
FIG. 3 shows bAngiogenin and hAngiogenin can induce myoblast differentiation into myotubes in the absence of serum in a dose dependant manner. C2C12 myoblast cells were cultured in 6 well plates in DMEM (control) supplemented with bAngiogenin (bANG) or hAngiogenin (hANG). The images taken after 96 hours show that both bANG and hANG induce myotube formation compared to the control DMEM culture.
Figure 4:
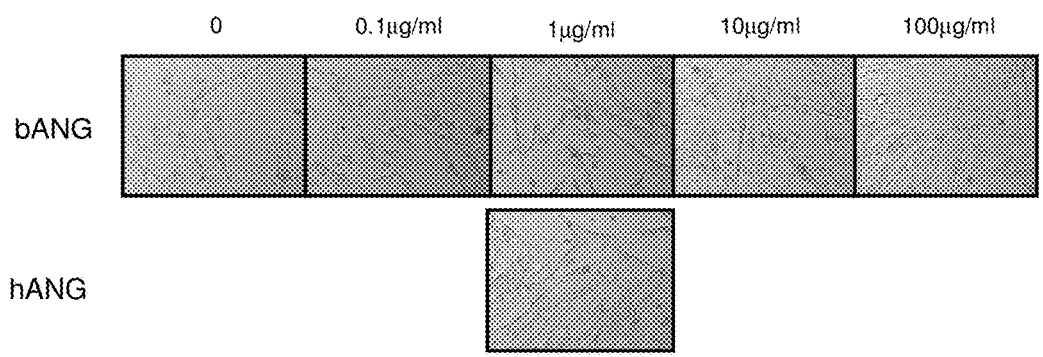
FIG. 4 shown bovine Angiogenin induces myotube formation in the presence of 2% HS in a dose dependant manner. C2C12 myoblast cells were cultured in differentiation media (DMEM+2% HS; control) supplemented with bAngiogenin (bANG) or hAngiogenin (hANG). The images taken after 96 hours show that bANG induces myotube formation compared to the control culture. rhANG proves that angiogenin is the inducing factor
Figure 5:
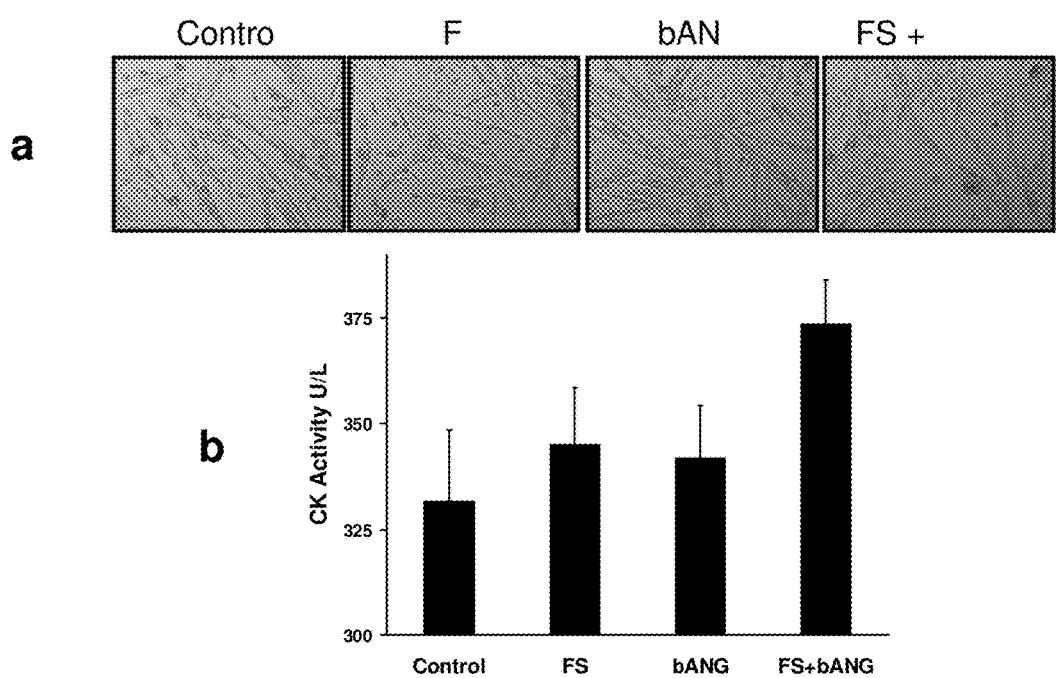
FIG. 5 shows bovine Angiogenin interacts with FS to enhance myotube formation. C2C12 myoblast cells were cultured in differentiation media (DMEM+2% HS; control) supplemented with bovine Angiogenin (bANG), Follistatin (FS) or combined. The images (a) and CK analysis (b) at 96 hours show that bANG interacts with FS to induces myotube formation synergistically compared to the either reagent in isolation.

100 ng of total RNA was amplified to produce biotin-labeled cDNA using the GeneChip® Whole Transcript (WT) Sense Target Labeling Assay (Affymetrix) as per the protocol provided by the manufacturer. Labelled cDNA was applied in recommended quantities to Mouse Gene 1.0 ST Arrays (Affymetrix) before being washed and stained using the Affymetrix 450 Fluidics Station and recommended solutions (Affymetrix). Scanning of the arrays was done on the Affymetrix GeneChip® Scanner 3000 7G before intensity data was extracted using Affymetrix GeneChip® Command Console (AGCC) software. The resultant .CEL files were used for data analysis in Partek® Genomics Suite ver. 6.4 (Partek), using default RMA normalisation and ANOVA The results of muscle cell differentiation experiments are shown in FIGS. 3, 4 and 5. FIG. 3 shows that under serum free non-differentiation conditions, bovine and rh angiogenin allow muscle cell differentiation to form myotubes. FIG. 4 shows that bAngiogenin also increases myoblast differentiation and myotube formation in the presence of 2% HS in a dose dependant manner. Inclusion of rhAngiogenin at a single dosage level proves that angiogenin is the inducing factor. FIG. 5 shows the synergistic effects of bovine angiogenin and rh follistatin. Under normal differentiation conditions, myotube size is increased following culture with bAngiogenin and rhFollistatin compared to standard conditions or culture with angiogenin or follistatin in isolation (FIG. 5a). Increased differentiation is proved by creatine kinase assays (5b) showing significantly higher levels in the angiogenin and rhFollistatin combination treatment compared to the treatments in isolation or the control.

Figure 6:
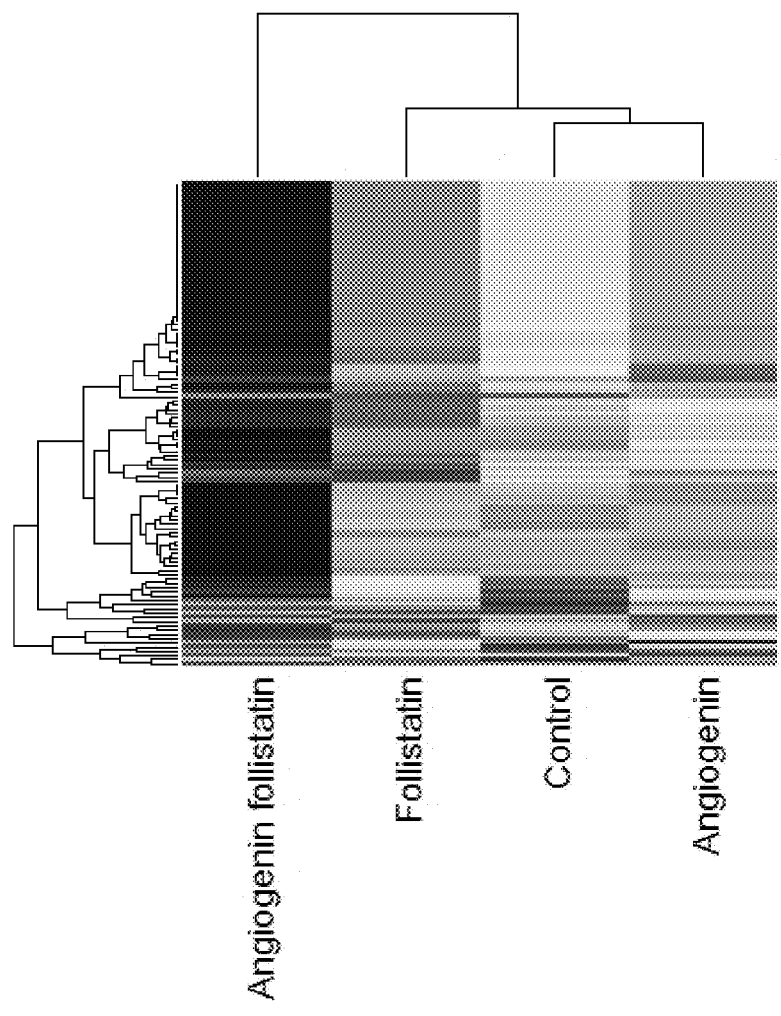
FIG. 6 shows hierarchical clustering of differentially expressed genes (based on a fold change of at least ±1.6 and P<0.05) in C2C12 cells after 2 hrs of differentiation to form myotubes. C2C12 myoblast cells were cultured in differentiation media (DMEM+2% HS; control) supplemented with bovine Angiogenin, Follistatin or combined Genes showing increased expression are represented in red, genes with decreased expression are represented in blue, genes with no change in expression are represented in yellow.

The synergistic effects of bAngiogenin and rhFollistatin on global gene expression profiles during the initial phase of myotubes formation (first 2 hours following differentiation) were tested using microarray analysis (FIG. 6). Minor differences in gene expression profiles are observed during initial myoblast differentiation in the control treatment or in presence of rhFollistatin or bAngiogenin. Marked differences are seen in the rhFollistatin and bAngiogenin combination treatment compared to the other treatments.

Figure 7:
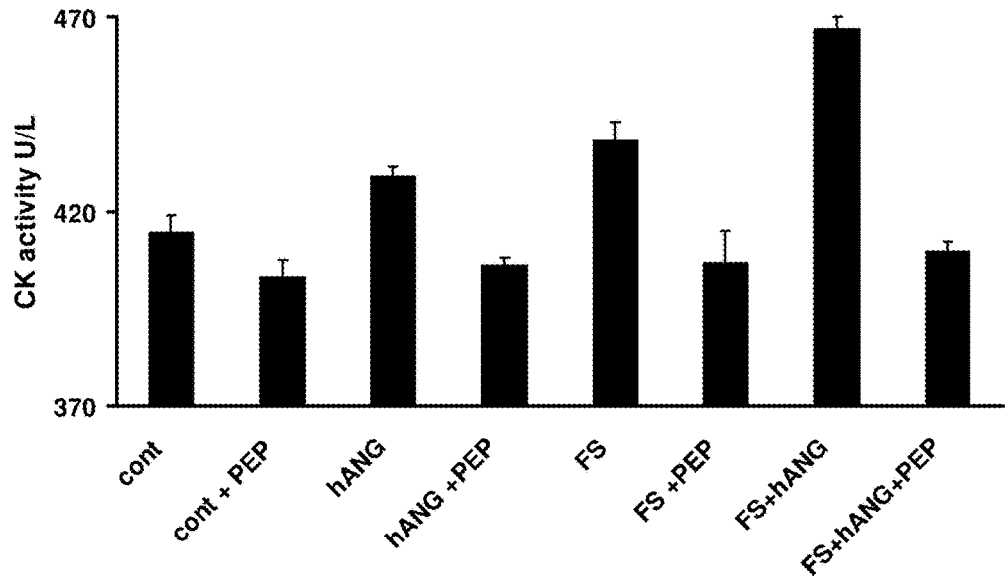
FIG. 7 shows Angiogenin Blocking Peptide inhibits myotube formation. The peptide (VFSVRVSILVF) specifically blocks the angiogenin/actin interaction and inhibits the angiogenin induction of myotube formation.

The specific role of angiogenin in the differentiation process was tested by repeating the differentiation culture conditions with the peptide VFSVRVSILVF (AUSPEP) which specifically blocks the angiogenin/actin interaction (FIG. 7). The angiogenin blocking peptide inhibited bAngiogenin specific differentiation as measured by increased creatine kinase activity compared to the control group, demonstrating that the response observed in FIG. 5 is due specifically to angiogenin.

Figure 8:
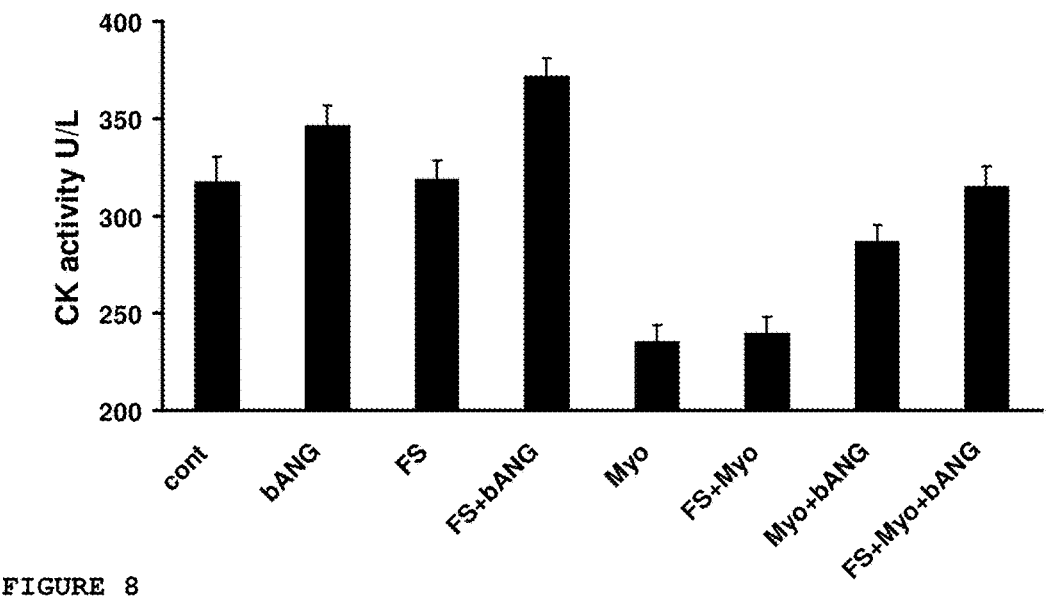
FIG. 8 shows bovine Angiogenin can regulate myostatin effects on myotube formation. Angiogenin is able to negate the negative effect of myostatin (Myo) on muscle myotube formation. The Angiogenin-Follistatin synergistic mechanism recovers tube formation to control levels in the presence of myostatin.
Figure 9:
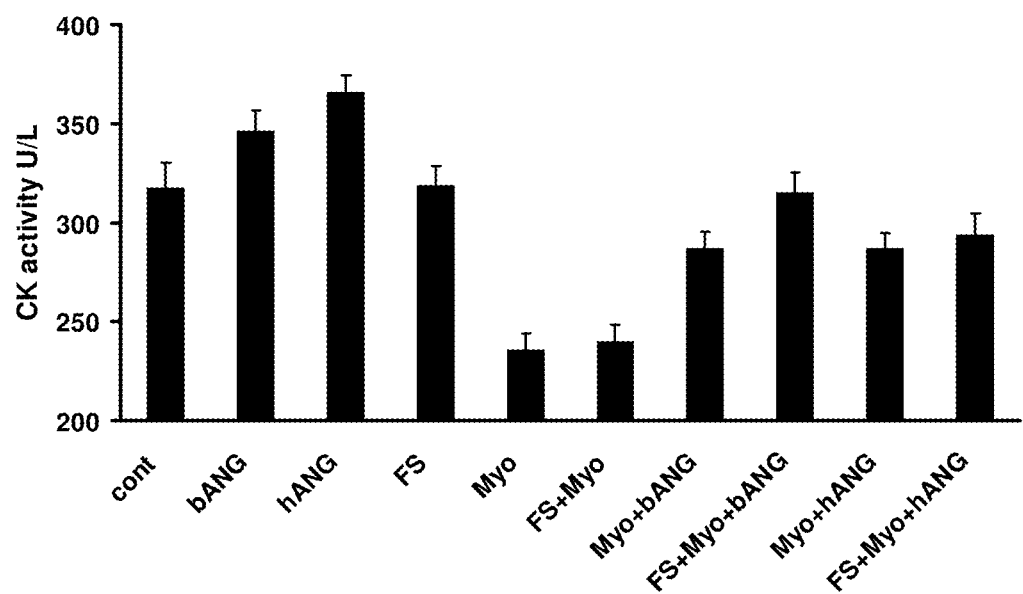
FIG. 9 shows angiogenin can regulate myostatin effects on myotube formation. Angiogenin is able to negate the negative effect of myostatin (Myo) on muscle myotube formation. The Angiogenin-Follistatin synergistic mechanism recovers tube formation to control levels in the presence of myostatin.

The ability of angiogenin to recover muscle cell differentiation was tested by incubating C2C12 muscle myoblasts with rhMyostatin, bAngiogenin and rhFollistatin under differentiation conditions. Myostatin is a negative regulator of muscle cell differentiation and inhibits binds with high affinity to follistatin. FIG. 8 demonstrates that myostatin inhibits muscle cell differentiation to myotubes and that follistatin alone can not recover cell differentiation. Including bAngiogenin in the incubation media recovered the majority of creatine kinase activity, however, the combination of bAngiogenin plus rhFollistatin recovered creatine kinase levels to the control levels, showing that angiogenin circumvents normal myostatin-follistatin cell differentiation signalling. This experiment was repeated using rhAngiogenin to prove the specificity of the mechanism to angiogenin (FIG. 9). This shows that using rhAngiogenin, the recovery of myostatin induced reduction in creatine kinase activity is identical to that of bAngiogenin, including the synergistic mechanism with follistatin.

Example 4: Angiogenin is Neuroprotective

Figure 10:
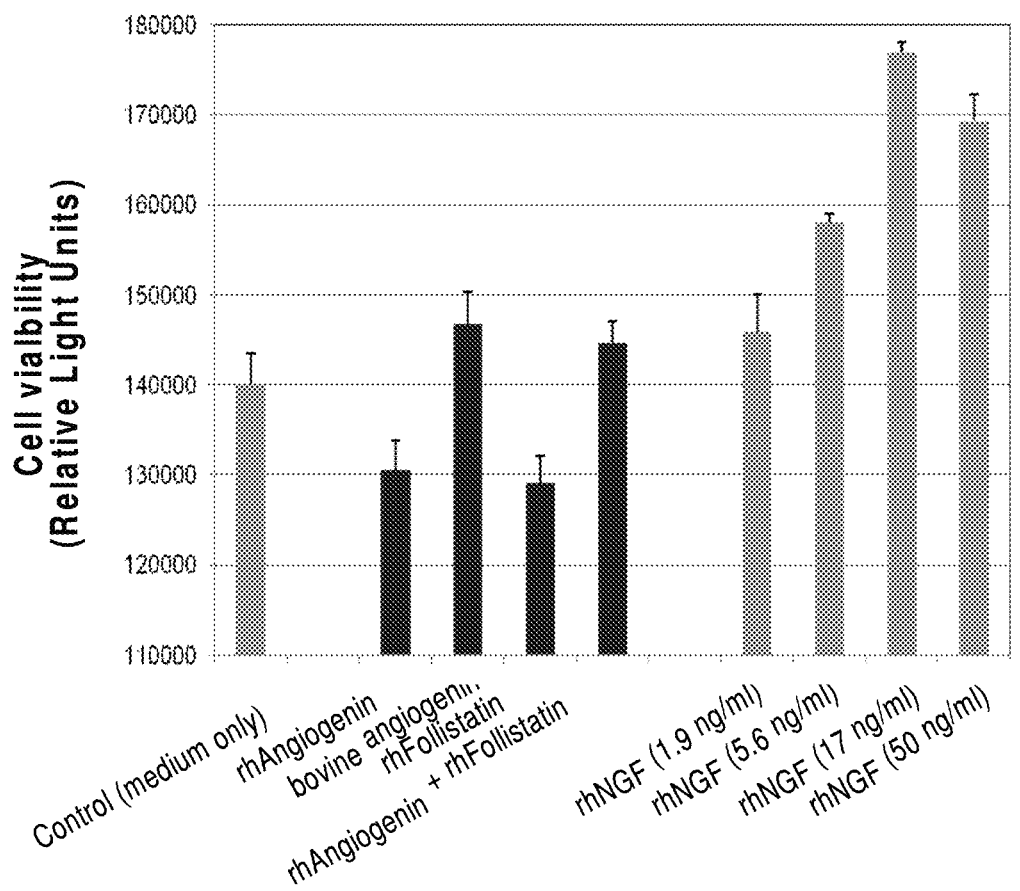
FIGS. 10 and 11 show protection of PC12 cells against cell death upon serum starvation in the presence of rhAngiogenin+rhFollistatin relative to rhAngiogenin alone or rhFollistatin alone. Results are presented as Mean+SEM of replicate cultures (12 replicates for medium only control; 6 replicates for rhAngiogenin (1.0 µg/ml), bAngiogenin (10 µg/ml) and rhFollistatin (0.1 µg/ml); 3 replicates for rhNGF controls).
Figure 11:
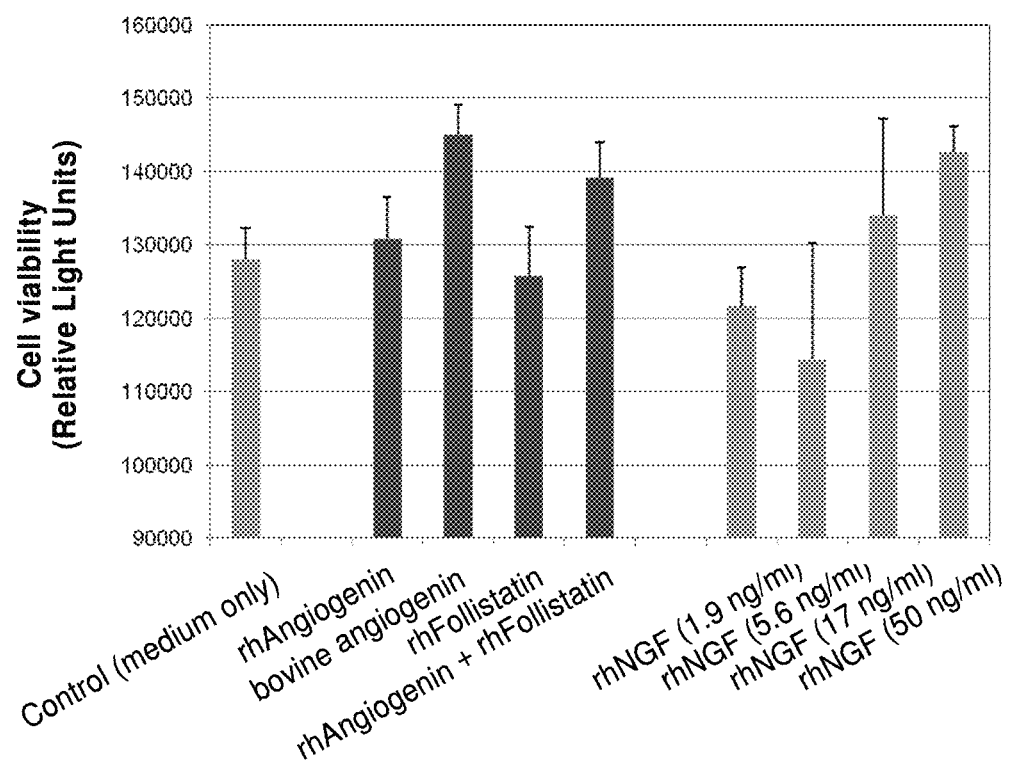
Figure 12:
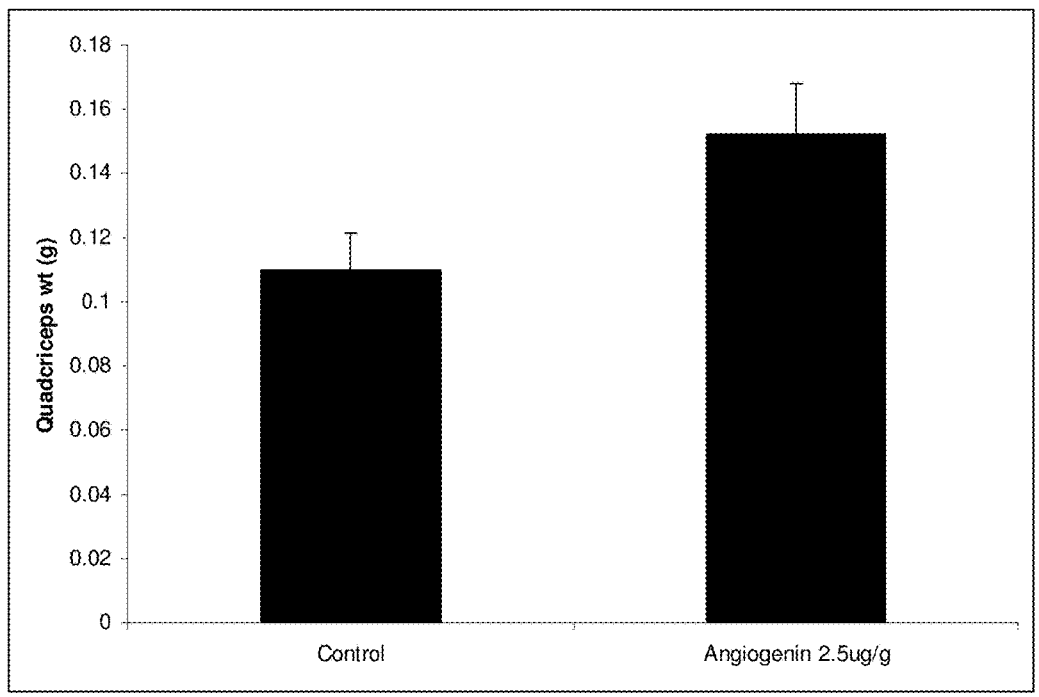
FIG. 12 shows angiogenin fed in the diet at 2.5 µg/g feed under ad libitum feeding conditions increases quadriceps weight in mice fed for 1 month and allowed to exercise freely on standard rodent running wheels.

To test if angiogenin was active in combination with follistatin on nerve cells PC12 cells were cultured with bAngiogenin, rhAngiogenin, and rhAngiogenin+rhFollistatin and cell survival measured in the absence of serum. FIG. 10 and FIG. 11 show protection of PC12 cells against cell death upon serum starvation in the presence of rhAngiogenin+rhFollistatin relative to rhAngiogenin alone or rhFollistatin alone. Bovine angiogenin also had a protective effect. After 22-24 hr of pre-treatment in the presence of treatments in complete medium (in DMEM with 10% horse serum and 5% heat-inactivated FBS), the cells were washed twice with 300 µl/well of serum free DMEM and addition of protein reagents. After three days of incubation, cell viability was measured based on ATP levels using CellTiterGlo® reagent (Promega, Madison, Wis.). Luminescence was read using a Victor3 (Perkin Elmer, Waltham, Mass.) multilabel plate reader at room temperature. FIG. 10 and FIG. 11 show protection of PC12 cells against cell death upon serum starvation.

Example 5: In Vivo Animal Studies

To analyse the in vivo effects of angiogenin on muscle phenotype in normal and muscular dystrophic mice animal studies were undertaken. All work was approved by the University of Western Australia animal ethics committee.

Mice were fed 2 diets during each trial; a control diet and a diet containing an bAngiogenin enriched fraction made according to example 1 at 2.5 µg/g mouse weight. These studies were carried out on adult (8 wks of age) male normal (C57) and dystrophic (mdx) mice with n=8 for each mouse strain per diet for each experiment.

Normal mice were subjected to a one month dietary period with ad libitum access to feed and voluntary exercise; for voluntary exercise a metal mouse wheel is placed inside the cage and the distance run by individual mice is recorded by a bicycle pedometer attached to the wheel. MDX mice were subjected to the same one month dietary period. In separate experiments, mdx mice were given the voluntary exercise treatment described above or were given no voluntary exercise wheel.

Experimental Analysis:

During the experiments body weight, amount of food eaten and muscle strength (grip strength test) were all measured twice weekly. At the conclusion of each experiment the mice were sacrificed by halothane anaesthesia and cervical dislocation.

Experimental mice were used for the following analysis to determine any changes in phenotype as a result of treatments on dystrophic and normal muscle.

1) Body Composition Analysis:

Half of each skinned mouse carcase were analysed for body composition. In addition, individual leg muscles including the quadriceps (quad), tibialis anterior (TA) and gastrocnemius muscles were dissected and weighed, as well as the abdominal fat pads and heart, data was recorded to determine gross phenotypic changes induced by the diets.

2) Histological Analysis:

Skeletal muscle and heart samples were collected and prepared for both frozen and paraffin histology. Histological analysis was performed on the following muscles, quad, TA and diaphragm. Haematoxylin and Eosin, Sudan Black and various immunohistological stains were performed on these muscles. Skeletal myofibre necrosis, myofibre hypertrophy and fat content of muscles was determined.

Results from the in vivo experiment are shown in FIGS. 12 to 15. It is clear that the diet supplemented with bAngiogenin enriched fraction at 2.5 µg/g induces muscle gain (FIG. 12) of up to 50% compared to the control group.

Figure 13:
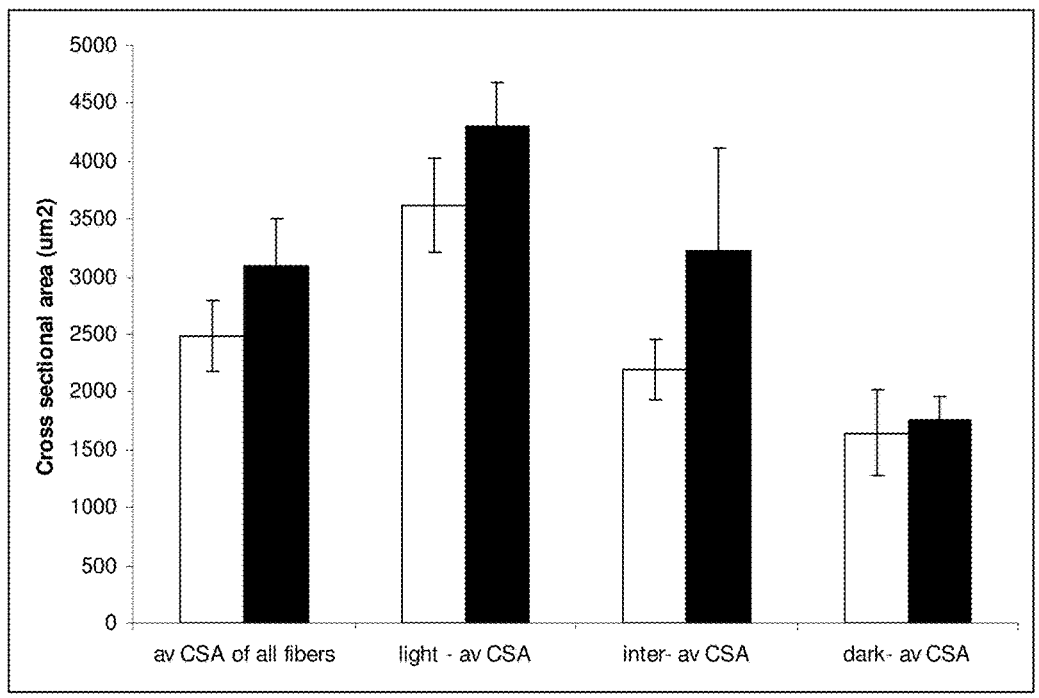
FIG. 13 shows that angiogenin fed in the diet at 2.5 µg/g feed under ad libitum feeding conditions increases results in muscle fibre type cross sectional area (SA) changes in mice fed for 1 month and allowed to exercise freely on standard rodent running wheels. Group means for control animals are represented in white bars and group means for angiogenin treated animals are represented in black bars. Standard deviations are given.
Figure 14:
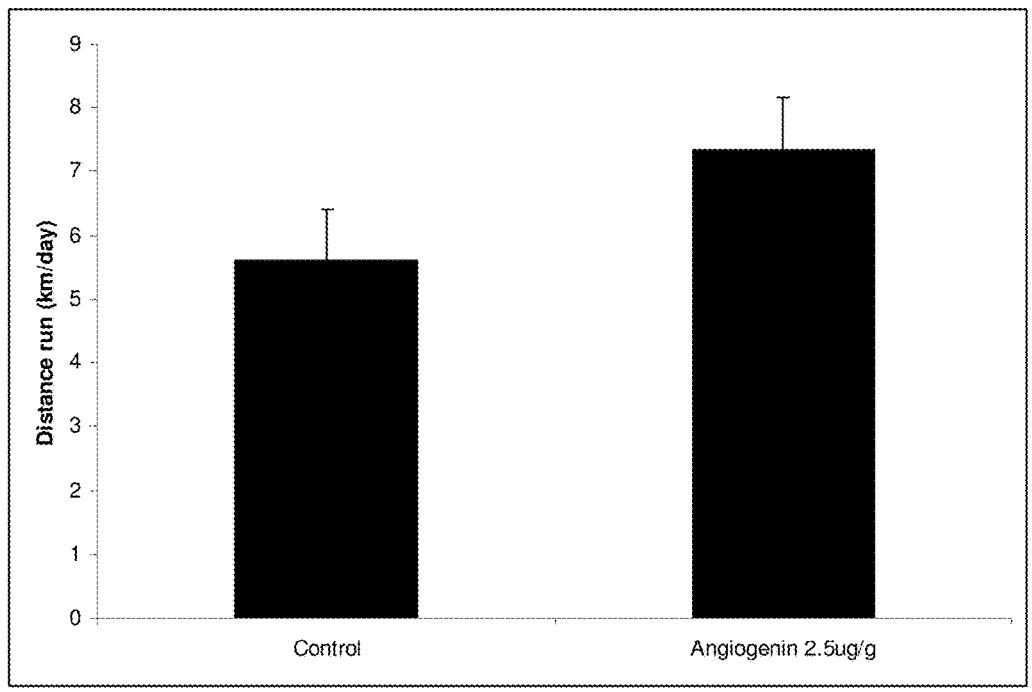
FIG. 14 shows that angiogenin fed in the diet at 2.5 µg/g feed under ad libitum feeding conditions increases distance run per day in mice fed for 1 month and allowed to exercise freely on standard rodent running wheels.

Increase in muscle mass was accommodated by increased cross sectional area of most muscle fibre types except for the population of small dark fibres corresponding to slow-twitch oxidative fibres (FIG. 13). Mice receiving the angiogenin enriched diet also ran 30% further than the control diet mice as measured by voluntary exercise (FIG. 14). Taken together, this data shows that angiogenin influences muscle size and fitness in vivo.

Figure 15:
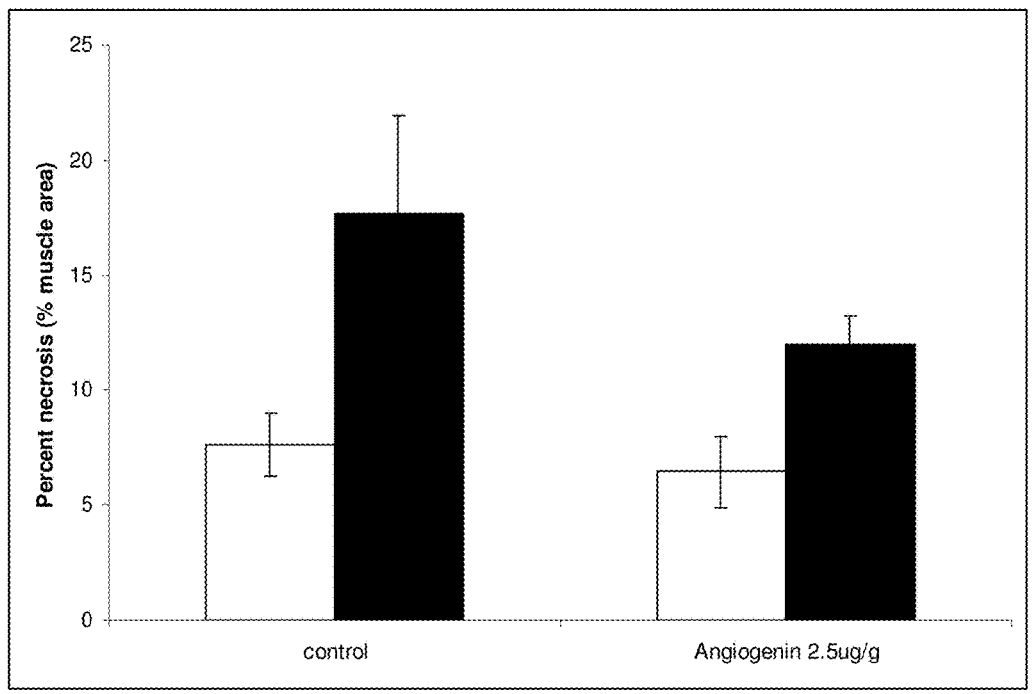
FIG. 15 shows that that angiogenin fed in the diet at 2.5 µg/g feed under ad libitum feeding conditions reduces the area of muscle necrosis in the quadriceps of MDX mice allowed to exercise freely on standard rodent running wheels.

When fed to mdx mice, angiogenin reduced the proportion of the muscle that was necrotic when mice were allowed access to voluntary exercise (FIG. 15). This demonstrates that angiogenin is capable of inhibiting the effects of exercise on muscle breakdown in mdx mice.

The invention claimed is:

1. A method of treating a subject having weakness or loss of weight caused by a disease or as a side effect of an illness, the method comprising administering to the subject in need thereof an effective amount of a composition comprising angiogenin, wherein the subject is a human, cat, dog, sports animal, food source animal, or avian species, and
wherein
the composition comprises angiogenin as the only active ingredient, or
the composition is a milk fraction in which the concentration of angiogenin is at least 10 times its concentration in milk and is depleted for lactoferrin and lactoperoxidase.

2. The method of claim 1, wherein the angiogenin is extracted from bovine milk.

3. The method of claim 1, wherein the angiogenin is administered orally without carriers or modification being required to allow for oral bioavailability.

4. The method of claim 1, wherein the angiogenin is administered in a food supplement or nutraceutical.

5. The method of claim 4, wherein the nutraceutical is provided in ready to consume liquid form.

6. The method of claim 4, wherein the nutraceutical is provided as a powdered composition.

7. The method of claim 1, wherein the angiogenin is recombinant angiogenin.

8. The method of claim 1, wherein the disease or illness is cancer.

9. The method of claim 1, wherein the disease or illness is congestive heart failure.

10. The method of claim 1, wherein the sports animal is a horse.

11. The method of claim 1, wherein the food source animal is a cow, pig or sheep.

12. The method of claim 1, wherein the avian species is a chicken, turkey, game bird or poultry.

13. A method of treating a subject having a wasting disorder, the method comprising administering to the subject in need thereof an effective amount of a composition comprising angiogenin, wherein the subject is a human, cat, dog, sports animal, food source animal, or avian species, and
wherein
the composition comprises angiogenin as the only active ingredient, or
the composition is a milk fraction in which the concentration of angiogenin is at least 10 times its concentration in milk and is depleted for lactoferrin and lactoperoxidase.

14. The method of claim 13, wherein the angiogenin is extracted from bovine milk.

15. The method of claim 13, wherein the angiogenin is administered orally without carriers or modification being required to allow for oral bioavailability.

16. The method of claim 13, wherein the angiogenin is administered in a food supplement or nutraceutical.

17. The method of claim 16, wherein the nutraceutical is provided in ready to consume liquid form.

18. The method of claim 16, wherein the nutraceutical is provided as a powdered composition.

19. The method of claim 13, wherein the angiogenin is recombinant angiogenin.

20. The method of claim 13, wherein the subject has cancer and the wasting disorder is cancer cachexia caused by the cancer.

21. The method of claim 13, wherein the subject has congestive heart failure and the wasting disorder is cardiac cachexia caused by a congestive heart failure.

22. The method of claim 13, wherein the sports animal is a horse.

23. The method of claim 13, wherein the food source animal is a cow, pig or sheep.

24. The method of claim 13, wherein the avian species is a chicken, turkey, game bird or poultry.

* * * * *